US012758965B2

(12) United States Patent
(10) Patent No.: US 12,758,965 B2
Carisbrooke et al.
(45) Date of Patent: Oct. 13, 2026

(54) CARTRIDGE FOR DETECTING TARGET ANALYTE

(71) Applicant: SEEGENE, INC., Seoul (KR)

(72) Inventors: Huw John Joseph Carisbrooke, Bentleigh East (AU); Anthony Joseph Stante, Edithvale (AU); Cameron Douglas Keller, Carlton (AU); Fernando Agostinho Peixoto Dias, Moonee Ponds (AU); Ross Murray, Olinda (AU); Stuart J Knowles, Oakleigh (AU); Richard John Louis Gardner, Ascot Vale (AU)

(73) Assignee: SEEGENE, INC., Seoul (KR)

( * ) Notice: Subject to any disclaimer, the term of this patent is extended or adjusted under 35 U.S.C. 154(b) by 715 days.

(21) Appl. No.: 17/975,734

(22) Filed: Oct. 28, 2022

(65) Prior Publication Data

US 2024/0139726 A1 May 2, 2024

(51) Int. Cl.

*B01L 3/00* (2006.01)
*B01L 7/00* (2006.01)
*C12Q 1/6806* (2018.01)

(52) U.S. Cl.

CPC ................. *B01L 3/502* (2013.01); *B01L 7/52* (2013.01); *C12Q 1/6806* (2013.01); *B01L 2200/026* (2013.01); *B01L 2200/10* (2013.01); *B01L 2200/16* (2013.01); *B01L 2300/0867* (2013.01); *B01L 2300/087* (2013.01); *B01L 2400/0478* (2013.01); *B01L 2400/0487* (2013.01); *B01L 2400/0622* (2013.01)

(58) Field of Classification Search

None

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 5,210,015 | A | 5/1993 | Gelfand et al. |
| 5,876,930 | A | 3/1999 | Livak et al. |
| 6,117,635 | A | 9/2000 | Nazarenko et al. |

(Continued)

FOREIGN PATENT DOCUMENTS

| | | | | |
|---|---|---|---|---|
| WO | WO-0078455 | A1 * | 12/2000 | .......... B01F 33/3017 |
| WO | WO-2011/037306 | A1 | 3/2011 | |

(Continued)

*Primary Examiner* — Matthew D Krcha

(74) *Attorney, Agent, or Firm* — Harness, Dickey & Pierce, P.L.C.

(57) ABSTRACT

According to the disclosure, a target analyte detection cartridge includes a sample chamber into which sample is inserted, a metering chamber connected to the sample chamber to meter a predetermined amount of sample, a mixing chamber connected to the metering chamber to receive a magnet bead, and a waste chamber connected to the metering chamber. The metering chamber has one side connected to each of the sample chamber and the mixing chamber and another side connected to the waste chamber. A first pneumatic flow path to which pneumatic pressure is provided is connected to a waste flow path that joins the other side of the metering chamber to connect the metering chamber and the waster chamber.

14 Claims, 6 Drawing Sheets

(56) References Cited

U.S. PATENT DOCUMENTS

| | | | | |
|---|---|---|---|---|
| 6,391,541 | B1 * | 5/2002 | Petersen | B01L 3/502 436/514 |
| 6,977,295 | B2 | 12/2005 | Belotserkovskii et al. | |
| 7,348,141 | B2 | 3/2008 | French et al. | |
| 7,537,886 | B1 | 5/2009 | Nazarenko et al. | |
| 2014/0176939 | A1 * | 6/2014 | Shah | G01N 21/8483 356/246 |
| 2016/0001283 | A1 * | 1/2016 | Carrano | B01L 3/502 422/522 |
| 2021/0047678 | A1 * | 2/2021 | Andeshmand | A61B 5/150961 |

FOREIGN PATENT DOCUMENTS

| | | | |
|---|---|---|---|
| WO | WO-2012/096523 | A2 | 7/2012 |
| WO | WO-2013/115442 | A1 | 8/2013 |
| WO | WO-2014/104818 | A1 | 7/2014 |

* cited by examiner

CARTRIDGE FOR DETECTING TARGET ANALYTE

FIELD

The disclosure relates to a cartridge for detecting a target analyte.

BACKGROUND

Nowadays people's interest in health increases and life expectancy extends. Thus, accurate analysis of pathogens and in vitro nucleic acid-based molecular diagnosis such as genetic analysis for a patient become significant, and the demand therefor is on the rise. Nucleic acid-based molecular diagnosis is performed by extracting nucleic acids from a sample and confirming whether a target nucleic acid is present in the extracted nucleic acids.

Polymerase chain reaction (PCR) is the most widely used nucleic acid amplification method, and the PCR process is performed by repeated cycling including denaturation of double-stranded DNA, annealing of oligonucleotide primers to the DNA templates and extension of primers by DNA polymerase (Mullis et al.; U.S. Pat. Nos. 4,683,195, 4,683,202 and 4,800,159; Saiki et al., (1985) Science 230, 1350-1354).

Real-time PCR using a fluorescent material is a method of detecting an increase in fluorescence intensity according to nucleic acid amplification during the PCR process. Real-time PCR enables multiplex detection by using different fluorescent dyes for each target; however, the technique requires expensive equipment and a lot of time for detection.

Meanwhile, recently, point of care testing which diagnoses patient's diseases quickly and correctly at any time and any place draws attention as a very significant technique of evidence-based precision health.

However, by the nature of the POC diagnostic device in which a simple and compact structure is critical, it is difficult to meet both fast processing and accurate detection.

SUMMARY

In the foregoing background, the disclosure provides a target analyte detection cartridge that allows the user to inject and use a sample without quantifying it.

To achieve the foregoing objectives, an aspect of the disclosure may provide a cartridge for detecting a target analyte, comprising: a sample chamber into which sample is inserted; a metering chamber connected to the sample chamber to meter a predetermined amount/a predetermined amount of sample; a mixing chamber connected to the metering chamber to receive a magnet bead; a waste chamber connected to the metering chamber; a plurality of buffer chambers connected to the mixing chamber to receive a buffer; a detection chamber connected to the mixing chamber to detect the target analyte; a metering flow path connecting the sample chamber and the metering chamber; a waste flow path connecting the metering chamber and the waste chamber; a mixing flow path connecting the metering chamber and the mixing chamber; a buffer flow path connecting the buffer chamber and the mixing chamber; a detection flow path connecting the mixing chamber and the detection chamber; a first pneumatic flow path communicating with a first pneumatic port; and a second pneumatic flow path communicating with a second pneumatic port, wherein a pre-processing region where the sample chamber, the metering chamber, the mixing chamber, and the buffer chambers are provided and a detection region where the detection chamber is provided are arranged in a horizontal direction, wherein in the pre-processing region, a chamber region, a valve region, and a buffer region are arranged in a vertical direction, and wherein in the chamber region, the sample chamber, the metering chamber, and the mixing chamber are arranged in the horizontal direction.

The cartridge may further comprise: a first valve controlling a fluid flow between the sample chamber and the metering chamber; a second valve controlling a fluid flow between the metering chamber and the mixing chamber; and a third valve controlling a fluid flow between the mixing chamber and the waste chamber, wherein in the valve region, the first value, the second valve, and the third valve are arranged in the horizontal direction.

The plurality of buffer chambers may include a lysis buffer chamber, a binding buffer chamber, a washing buffer chamber, and an elution buffer chamber, and wherein in the buffer region, the plurality of buffer chambers may be arranged in the horizontal direction.

In the pre-processing region, the sample chamber, the metering chamber, and the mixing chamber may be sequentially disposed.

The sample chamber may have a shape in which a width in the vertical direction is larger than a width in the horizontal direction and includes an injection space provided in an upper portion of the sample chamber in the vertical direction and a liquid delivery space provided in a lower portion of the sample chamber in the vertical direction and connected to the metering chamber.

The metering chamber may have a shape in which a width in the vertical direction is larger than a width in the horizontal direction, and wherein an upper portion of the metering chamber in the vertical direction is connected to the waste flow path, and a lower portion of the metering chamber in the vertical direction is connected to each of the sample chamber and the mixing chamber.

A plurality of detection chambers may be arranged side by side in the vertical direction.

In the pre-processing region, the chamber region, the valve region, and the buffer region may be sequentially disposed.

The waste chamber may be positioned lower than the sample chamber, the metering chamber, and the mixing chamber in the vertical direction.

A waste region where the waste chamber is provided may be disposed below the buffer region.

The plurality of buffer chambers may be disposed lower than the sample chamber, the metering chamber, and the mixing chamber in the vertical direction and may be positioned higher than the waste chamber in the vertical direction.

One side of the metering chamber may be connected to each of the sample chamber and the mixing chamber, and another side thereof be connected to the waste chamber, and wherein the first pneumatic flow path may be join the other side of the metering chamber and then be connected to the waste flow path.

The cartridge may further comprise a mastermix chamber provided in the pre-processing region and have one side connected to the mixing chamber and another side connected to the detection chamber.

The first pneumatic flow path may be divided into a first branch connected to the metering chamber and the waste chamber and a second branch connected to the mastermix chamber, and wherein the second pneumatic flow path may be connected to the mixing chamber.

The cartridge may further comprise: a mastermix chamber provided in the pre-processing region and having one side connected to the mixing chamber and another side connected to the detection chamber; a fourth valve controlling a fluid flow between the mixing chamber and the master mix chamber; and a fifth valve controlling a fluid flow between the mastermix chamber and the detection chamber.

In the pre-processing region, the sample chamber, the metering chamber, the mixing chamber, the master mix chamber, and the buffer chamber may be provided in the horizontal direction, wherein in the chamber region, the sample chamber, the metering chamber, the mixing chamber, and the mastermix chamber may be provided in the vertical direction, wherein in the valve region, the first value, the second valve, the third valve, the fourth valve, and the fifth valve may be arranged in the horizontal direction, and wherein in the buffer region, the plurality of buffer chambers may be arranged in the horizontal direction.

According to an embodiment of the disclosure, it is possible to reduce detection time by simplifying the manual sample quantification step.

It is also possible to shorten processing time while enhancing detection accuracy thanks to the capability of precise and fast sample metering through an air knife process.

A quantity of reagent may quickly be supplied using a blister pouch, and the reagent remaining in the conduit may be moved to the mixing chamber through air blow.

It should be appreciated that the effects of the disclosure are not limited thereto, but may rather include all effects inferable from the configuration of the disclosure described in the detailed description or the claims of the disclosure.

BRIEF DESCRIPTION OF DRAWINGS

The above and other objects, features, and advantages of the disclosure will be more clearly understood from the following detailed description, taken in conjunction with the accompanying drawings, in which.

DETAILED DESCRIPTION

Figure 1:
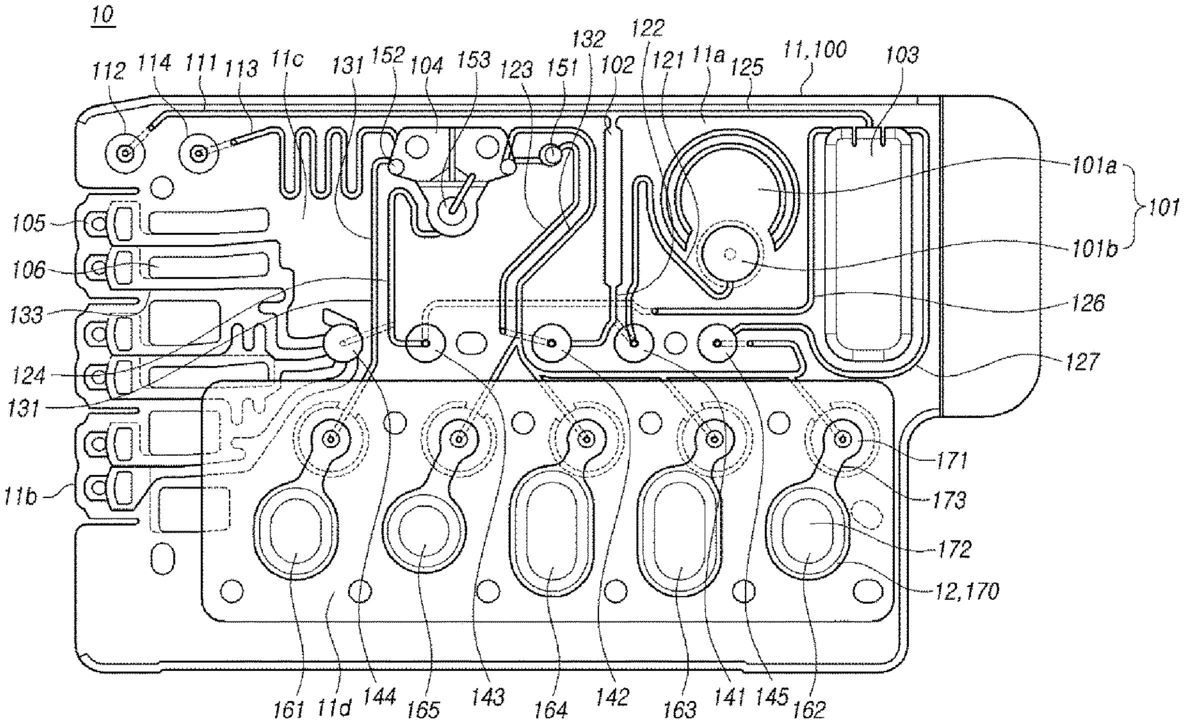
FIG. 1 is a plan view illustrating a cartridge according to an embodiment of the disclosure.

Hereinafter, the disclosure will be explained with reference to embodiments and example drawings. The embodiments are for illustrative purposes only, and it should be apparent to a person having ordinary knowledge in the art that the scope of the disclosure is not limited to the embodiments.

In addition, in adding reference numerals to the components of each drawing, it should be noted that same reference numerals are assigned to same components as much as possible even though they are shown in different drawings. In addition, in describing the embodiments of the disclosure, when it is determined that a detailed description of a related well-known configuration or function interferences with the understanding of the embodiments of the disclosure, the detailed description thereof will be omitted.

In addition, in describing the components of the embodiments of the disclosure, terms such as first, second, A, B, (a), (b), (i), (ii), etc. may be used. These terms are only for distinguishing the components from other components, and the nature or order of the components is not limited by the terms. When a component is described as being "connected," "coupled" or "fastened" to other component, the component may be directly connected or fastened to the other component, but it will be understood that another component may be "connected," "coupled" or "fastened" between the components.

The disclosure relates to an apparatus for detecting a target analyte in a sample.

As used herein, the term "sample" may include a biological sample (e.g., cells, tissues and fluids from a biological source) and a non-biological sample (e.g., food, water and soil). Examples of the biological sample may include viruses, bacteria, tissues, cells, blood (e.g., whole blood, plasma and serum), lymph, bone marrow fluid, salvia, sputum, swab, aspiration, milk, urine, feces, ocular fluid, semen, brain extract, spinal fluid, joint fluid, thymus fluid, bronchoalveolar lavage fluid, ascites and amniotic fluid. Also, the sample may include natural nucleic acid molecules isolated from a biological source and synthetic nucleic acid molecules. According to an embodiment of the disclosure, the sample may include an additional substance such as water, deionized water, saline solution, pH buffer, acid solution or alkaline solution.

A target analyte refers to a substance that is the subject of analysis. The analysis may mean obtaining information on, for example, the presence, amount, concentration, sequence, activity or property of the analyte in the sample. The analyte may include various substances (e.g., biological substance and non-biological substance such as compounds). Specifically, the analyte may include a biological substance such as nucleic acid molecules (e.g., DNA and RNA), proteins, peptides, carbohydrates, lipids, amino acids, biological compounds, hormones, antibodies, antigens, metabolites or cells. According to an embodiment of the disclosure, the analyte may be nucleic acid molecules.

The apparatus for detecting a target analyte of the disclosure may be an apparatus for detecting a target nucleic acid. The apparatus for detecting a target nucleic acid allows a nucleic acid reaction to be performed in a sample, to detect a target nucleic acid.

The nucleic acid reaction refers to sequential physical and chemical reactions which generate a signal depending on the presence of a nucleic acid of a specific sequence in the sample or the amount thereof. The nucleic acid reaction may include the binding of a nucleic acid of a specific sequence in a sample to other nucleic acids or substances, or replication, cleavage or decomposition of a nucleic acid of a specific sequence in the sample. The nucleic acid reaction may involve a nucleic acid amplification reaction. The nucleic acid amplification reaction may include amplification of a target nucleic acid. The nucleic acid amplification reaction may specifically amplify the target nucleic acid.

The nucleic acid reaction may a signal-generation reaction which can generate a signal depending on the presence/absence of a target nucleic acid in the sample or the amount thereof. The signal-generation reaction may be a technique of genetic analysis such as PCR, real-time PCR or microarray.

Various methods for generating an optical signal which indicates the presence of a target nucleic acid using a nucleic acid reaction are known. Representative examples thereof include the following: TaqMan™ probe method (U.S. Pat. No. 5,210,015), molecular beacons method (Tyagi et al., Nature Biotechnology v.14 Mar. 1996), scorpion method (Whitcombe et al., Nature Biotechnology 17:804-807 (1999)), sunrise or amplifluor method (Nazarenko et al., 2516-2521 Nucleic Acids Research, 25(12):2516-2521 (1997), and U.S. Pat. No. 6,117,635), lux method (U.S. Pat. No. 7,537,886), CPT (Duck P, et al., Biotechniques, 9:142-148(1990)), LNA method (U.S. Pat. No. 6,977,295), plexor method (Sherrill C B, et al., Journal of the American Chemical Society, 126:4550-4556(2004)), Hybeacons™ (D. J. French, et al., Molecular and Cellular Probes (2001) 13, 363-374 and U.S. Pat. No. 7,348,141), dual-labeled, self-quenched probe (U.S. Pat. No. 5,876,930), hybridization probe (Bernard P S, et al., Clin Chem 2000, 46, 147-148), PTOCE (PTO cleavage and extension) method (WO 2012/096523), PCE-SH (PTO Cleavage and Extension-Dependent Signaling Oligonucleotide Hybridization) method (WO 2013/115442), PCE-NH (PTO Cleavage and Extension-Dependent Non-Hybridization) method (PCT/KR2013/012312) and CER method (WO 2011/037306).

An apparatus for detecting a target analyte according to an embodiment of the disclosure may be an apparatus for detecting a nucleic acid, and may detect a signal generated depending on the presence of the target nucleic acid. The apparatus for detecting a nucleic acid may amplify and detect a signal with nucleic acid amplification. Alternatively, the apparatus for detecting a nucleic acid may amplify and detect a signal without nucleic acid amplification. Preferably, the apparatus for detecting a nucleic acid detects a signal with nucleic acid amplification.

An apparatus for detecting a target analyte according to an embodiment of the disclosure may comprise a nucleic acid amplifier.

A nucleic acid amplifier refers to an apparatus for performing a nucleic acid amplification reaction which amplifies a nucleic acid having a specific nucleotide sequence. Examples of the method for amplifying a nucleic acid include polymerase chain reaction (PCR), ligase chain reaction (LCR) (U.S. Pat. Nos. 4,683,195 and 4,683,202; PCR Protocols: A Guide to Methods and Applications (Innis et al., eds, 1990)), strand displacement amplification (SDA) (Walker, et al. Nucleic Acids Res. 20(7):1691-6 (1992); Walker PCR Methods Appl 3(1):1-6 (1993)), transcription-mediated amplification (Phyffer, et al., J. Clin. Microbiol. 34:834-841 (1996); Vuorinen, et al., J. Clin. Microbiol. 33:1856-1859 (1995)), nucleic acid sequence-based amplification (NASBA) (Compton, Nature 350(6313):91-2 (1991)), rolling circle amplification (RCA) (Lisby, Mol. Biotechnol. 12(1):75-99 (1999); Hatch et al., Genet. Anal. 15(2):35-40 (1999)) and Q-beta Replicase (Lizardi et al., BiolTechnology 6:1197 (1988)), etc.

An apparatus for detecting a target analyte according to an embodiment of the disclosure may be an apparatus for performing a nucleic acid amplification reaction with temperature changes. For example, the nucleic acid amplifier may carry out a denaturing step, an annealing step and an extension (or elongation) step to amplify deoxyribonucleic acid (DNA) having a specific base sequence.

In the denaturing step, a sample and reagent solution containing double-stranded DNA templates is heated to a specific temperature, for example about 95° C., to separate double-stranded DNA into single-stranded DNA. In the annealing step, an oligonucleotide primer having a nucleotide sequence complementary to the nucleotide sequence of a nucleic acid to be amplified is provided, and the primer and the separated single-stranded DNA are cooled down to a specific temperature, for example 60° C., to promote the primer binding to the specific nucleotide sequence of the single-stranded DNA to form a partial DNA-primer complex. In the extension step, the solution is maintained at a specific temperature, for example 72° C., after the annealing step to form double-stranded DNA by DNA polymerase based on the primer of the partial DNA-primer complex.

The aforementioned three steps are repeated, for example 10 to 50 times, geometrically amplifying DNA having the specific nucleotide sequence. In some cases, the nucleic acid amplifier may perform the annealing step and extension step simultaneously. In this case, the nucleic acid amplifier may complete one cycle by performing two steps including a denaturing step and an annealing/extension step.

Particularly, an apparatus for detecting a target analyte according to an embodiment may be an apparatus for performing a nucleic acid amplification reaction with temperature changes and a reaction of generating an optical signal depending on the presence of a nucleic acid and detecting the generated optical signal.

Also, an apparatus for detecting a target analyte according to an embodiment may comprise an optical module, a thermal module, a controller for controlling the modules, a frame for supporting the optical module and thermal module, a case for enclosing the components and a display unit.

The optical module may comprise an optical housing for forming a dark room, a light source for generating excitation light, an excitation light filter unit for providing a wavelength range of a target analyte, a beam splitter for setting a light path and a detection unit for detecting emission light from a sample. The optical module may further comprise a heat lead for pressing and heating a cover of a reaction vessel (e.g., tube or cartridge) accommodated in a thermal block.

The excitation light filter unit may comprise an excitation light filter wheel having a plurality of filters with different wavelength ranges and a drive unit for driving the excitement light filter wheel.

The detection unit may comprise a detection sensor for obtaining images from emission light, an emission light filter unit and an emission light lens array for adjusting the light path and focus.

The emission light filter unit may comprise an emission light filter wheel having a plurality of filters with different wavelength ranges and a drive unit for driving the emission light filter wheel.

The thermal module may comprise a thermal block in which a reaction vessel is accommodated or a reaction vessel is seated, a thermal unit comprising a thermal element, a cooling unit for cooling the thermal block and a thermal block housing.

The cooling unit may comprise a heat radiating plate and a cooling fan.

Next, the operation of an apparatus for detecting a target analyte according to an embodiment is described.

A light source emits light to excite a fluorescent substance included in a sample. An example of the light source may be a light emitting diode (LED).

The light emitted from the light source may be indicated as an excitation beam, and the light emitted from the sample may be indicated as an emission beam. The path of the excitation beam emitted from the light source may be indicated as an excitation path, and the path of the emission beam emitted from the sample may be indicated as an emission path.

A beam splitter may selectively reflect or transmit incident light. The excitation light of the light source penetrates the beam splitter and passes through a hole of a heat lead to arrive at a reaction vessel accommodated in a thermal block.

The light emitted from the sample is reflected at the beam splitter and passes through an emission light lens array to arrive at a detection sensor.

A thermal block may be a thermally conductive material. When the thermal block is in contact with reaction vessels, heat may be transferred from the thermal block to the reaction vessels. The thermal block may be made of, for example, metal such as aluminum, gold, silver, nickel or copper.

A thermal block housing may accommodate the thermal block, thermal element, cooling unit, etc.

A thermal element may increase or decrease the temperature of the thermal block. The thermal element is disposed below the thermal block and is in contact with the thermal block to transfer heat to the thermal block or absorb heat from the thermal block. For example, the thermal element may be a Peltier element or a heating wire, and comprise an FPCB to which the element is connected.

A cooling unit may be disposed below the thermal block, and comprise a heat radiating plate or a heat radiating fin for emitting heat to the outside of the thermal block. Also, the cooling unit may comprise a cooling fan for providing the air to cool the heat radiating plate or heat radiating fin.

A detection unit detects a signal from the sample. Specifically, the detection unit comprises a detection sensor for detecting fluorescence generated from the sample. The detection sensor may be a charge coupled device (CCD), complementary metal oxide semiconductor (CMOS), field effect transistor or photodiode.

An apparatus for detecting a target analyte according to an embodiment comprises a sample holder, a light emitting module and a detection module.

A sample refers to a substance in which a target analyte is to be detected. The sample includes a biological sample (e.g., cells, tissues and fluids from a biological source) and a non-biological sample (e.g., food, water and soil). Examples of the biological sample include, but are not limited to, viruses, bacteria, tissues, cells, blood, plasma, serum, lymph, sputum, swab, aspiration, bronchoalveolar lavage fluid, milk, urine, feces, ocular fluid, salvia, semen, brain extract, spinal fluid (SCF), extracts of appendix, spleen and tonsil tissues, ascites and amniotic fluid. Also, the sample may include natural nucleic acid molecules isolated from a biological source and synthetic nucleic acid molecules.

The sample according to the disclosure may include a substance necessary for detecting a target analyte. For example, the sample may include an additional substance such as water, deionized water, saline solution, pH buffer, acid solution or alkaline solution. According to an embodiment of the disclosure, the sample may include an optical probe. The optical probe refers to a probe which generates an optical signal depending on the presence of a target nucleic acid. The optical probe may be a fluorescent probe. The fluorescent probe as used herein may include any molecules known in the art.

The light emitting module according to the disclosure supplies a proper optical stimulus to a sample contained in the sample holder, and the detection module senses an optical signal generated from the sample in response thereto.

The optical signal may be a luminescence signal, phosphorescence signal, chemiluminescence signal, fluorescence signal, polarized fluorescence signal or other colored signal. The optical signal may be generated in response to an optical stimulus given to the sample.

The sample holder has a sample containing part for containing the sample. The sample holder is a component for containing the sample directly in the sample containing part or accommodating a reaction vessel containing the sample.

As used herein, the expression "the sample holder may contain the sample" may be used to comprehensively include the cases where the sample holder contains the sample directly in the sample containing part or accommodates the reaction vessel containing the sample.

The sample holder allows the sample to be placed in a predetermined position, such that an optical stimulus from a light emitting module arrives at the sample and an optical signal generated from the sample arrives at a detection module.

Heat may be supplied to the sample holder by a heat generating element, and heat is transferred to the sample contained directly in the sample holder or the sample contained in the reaction vessel.

The reaction vessel may be made of various materials, for example, plastic, ceramic, glass or metal.

The sample holder for accommodating a reaction vessel may be in the shape of a block or plate. The sample holder for accommodating a reaction vessel may include a recess, for example a well, for accommodating the reaction vessel or have a flat surface. The sample holder for accommodating a reaction vessel may have a structure of guiding the position of the reaction vessel or fixing the reaction vessel thereto.

A sample holder is configured to contain at least one sample.

One of the representative examples of the sample holder for accommodating a reaction vessel is a heat block. The heat block includes a plurality of wells or holes, and reaction vessels may be accommodated in the wells or holes.

The sample holder accommodating sample reaction vessels means a state in which sample reaction vessels are placed in a plurality of wells of the sample holder or are arranged in assigned positions on the sample holder.

A reaction vessel is used for containing a sample to be analyzed, and includes vessels of a variety of shapes, for example a tube, vial, strip in which a plurality of single tubes are connected, plate in which a plurality of tubes are connected, microcard, chip, cuvette or cartridge.

The sample holder for directly containing the sample may have a shape of the reaction vessel as described above, and be made of the material of the reaction vessel as described above.

According to an embodiment, the sample holder may be made of a material having a thermal conductivity. When the sample holder is in direct contact with the sample or is in contact with reaction vessels, heat may be transferred to the sample or the sample in the reaction vessels from the sample holder.

The sample holder may be made of metal such as aluminum, gold, silver, nickel or copper, plastic or ceramic.

The sample holder is configured to contain a plurality of samples, and adjusts the temperature of the plurality of samples to cause a reaction for detection such as a nucleic acid amplification reaction. For example, in the case where the sample holder is a heat block having a plurality of wells, the sample holder is formed as one heat block, and each well of the heat block may be configured not to be thermally independent from each other. In this case, all wells of the sample holder in which the samples are contained have the same temperature, and the temperatures of the contained samples cannot be adjusted independently according to different protocols.

Alternatively, the sample holder may be configured to adjust the temperatures of some of the samples in the sample holder according to different protocols. The sample holder may have two or more reaction regions that are thermally independent from each other. Each of the reaction regions is thermally independent. Heat is not transferred from one reaction region to other reaction regions. An insulating material or an air gap may be present between the reaction regions. The temperatures of the reaction regions may be controlled independently. Reaction protocols including temperature and time may be set individually for each of the reaction regions, and each of the reaction regions may perform a reaction according to the individually set protocols. As such, reactions are performed in the reaction regions according to the individually set protocols, and thus the time points of detecting light in the reaction regions are independent from each other.

Hereinafter, the directions used are set with respect to the drawings. For example, the cartridge 10 is seated on the detection device in a standing state in which the top of the figure is positioned up and is moved to the left of the figure to be mounted.

FIG. 1 is a plan view illustrating a cartridge 10 according to an embodiment of the disclosure.

Referring to FIG. 1, a cartridge 10 of a target analyte detection device according to an embodiment of the disclosure may include a base 11 having a plurality of chambers and flow paths, a cover (transparent) sealing one or two opposite surfaces of the base 11, and a blister chamber unit 12 fluidly coupled to the base 11 to provide a buffer.

The blister chamber unit 12 may be provided as a member separate from the base 11 and fluidly connected thereto, or may be provided as part of the base 11. An embodiment in which the blister chamber unit 12 is provided as a separate member from the base 11 is described below.

The base 11 may include a sample chamber 101 into which sample is inserted or for receiving a sample, a metering chamber 102 for metering a predetermined amount of sample or a quantity of sample, a waste chamber 103 for storing the wasted fluid, a mixing chamber 104 for mixing the sample with a reagent and where an elution reaction occurs, and a detection chamber 105 where a sample detection reaction (e.g., PCR reaction) and target analyte detection occur.

The base 11 may form flow paths for connecting the chambers and may include valves for opening and closing the flow paths.

The base 11 may be a plate-shaped base plate 100. The base plate 100 may have a chamber, flow path, and valve on one surface thereof. Alternatively, the base plate 100 may have a chamber, flow path, and valve on two opposite surfaces thereof. For example, if flow paths are formed on two opposite surfaces of the base plate 100, the flow paths may cross each other on the different surfaces, allowing for a flow path design of various paths. Any flow paths may be provided on both the two opposite surfaces of the base plate 100 and be connected to each other through the base plate 100.

The base 11 may be provided to move in one direction (left direction in the drawings) to be mounted with respect to the target analyte detection device (not shown). For example, a rack is formed on a side edge (upper portion in the drawings) of the base 11, and the rack of the base 11 may be mechanically coupled with the pinion of the driving module provided in the target analyte detection device so that as the pinion rotates, the base 11 may move in one direction (left direction in the drawings). The base 11 may slide in one direction by use of various mechanical structures, e.g., a piston structure, as well as the rack-pinion structure, and may not only slide but also pivot, rotate, or swing.

The cover may be coupled to one surface of the base 11 to seal any one or more of the chamber, flow path, and valve formed on one surface (front surface in the drawings) of the base 11. Alternatively, if the chamber, flow path, and valve are formed on the two opposite surfaces of the base 11, the cover may be coupled to each of the two opposite surfaces of the base 11 to seal one or more of them. For example, the cover may include a first cover to seal one surface (front surface in the drawings) of the base 11 and a second cover to seal the other surface (back surface in the drawings) of the base 11.

The cover includes a membrane coupled to one surface of the base 11. As an example, the cover membrane may be provided as a metal membrane including aluminum foil or polymer membrane. The cover may be formed of other various materials and may also be provided as a plate, not as a membrane. The cover membrane may be coupled to the base 11 via, e.g., thermal compression, an adhesive, or mechanical coupling.

In another embodiment, in the cartridge, the base and cover both may be provided as plates, and any one or more of the chamber, flow path, and valve may be formed on the cover plate. Any one or more of the chamber, flow path, and valve may be formed on all of the base and the cover plate.

According to an embodiment, the target analyte cartridge 10 may provide an air pressure to the flow path, moving the fluid. The base plate 100 may include a pneumatic flow path communicating with the fluid flow path. The pneumatic flow path may be connected to a pneumatic means for providing positive or negative pressure. As an example, the pneumatic means includes a pump.

The pneumatic flow path may include a first pneumatic flow path 111 and a second pneumatic flow path 113. Further, the first and second pneumatic flow paths 111 and 113 may be selectively used as air injection flow paths or as air discharge flow paths. For example, the first and second pneumatic flow paths 111 and 113 may be connected to the pump through a direction switching means, such as a solenoid valve.

When the solenoid valve is in a first position, the first pneumatic flow path 111 may be used as an air injection flow path, and the second pneumatic flow path 113 may be used as an air discharge flow path. Conversely, when the solenoid valve is in a second position, the first pneumatic flow path 111 may be used as an air discharge flow path, and the second pneumatic flow path 113 may be used as an air injection flow path. As such, the direction of the fluid flow may be adjusted by switching the direction of the pressure provided to the first pneumatic flow path 111 and the second pneumatic flow path 113.

The cover membrane may include pneumatic ports 112 and 114 for opening the pneumatic flow paths. The pneumatic ports 112 and 114 may include a first pneumatic port 112 connected to the first pneumatic flow path 111 and a second pneumatic port 114 connected to the second pneumatic flow path 113.

The meaning of opening or closing the pneumatic ports 112 and 114 may include the meaning of operating or stopping the pneumatic means connected to the pneumatic ports 112 and 114. The meaning of providing pneumatic pressure to the pneumatic ports 112 and 114 may include the meaning of operating the pneumatic means connected to the pneumatic ports 112 and 114 to transfer the pneumatic pressure to the pneumatic flow paths 111 and 113.

Meanwhile, the target analyte cartridge 10 may include a pre-processing region 11*a* where the injected sample is pre-processed and a detection region 11*b* which fluidly communicates with the mixing chamber 104, which is the last stage of the pre-processing region 11*a*, and where detection of the target material occurs. For example, the pre-processing region 11*a* may be provided on the right side of the cartridge 10, and the detection region 11*b* may be provided on the left side of the cartridge 10. The sample injected into the cartridge 10 is moved through the pre-processing region 11*a* to the detection region 11*b*, and is generally moved from the left to the right of the cartridge 10.

Further, the target analyte cartridge 10 may include a sample flow region 11*c* including a chamber and a flow path through which the sample flows and a blister chamber region 11*d* in which the blister chamber is provided. The target analyte cartridge 10 may include a valve region where a valve for opening/closing the flow of the fluid between the sample flow region 11*c* and the blister chamber region 11*d* is provided. For example, the sample flow region 11*c* may be provided in an upper portion of the cartridge 10, and the blister chamber region 11*d* may be provided in a lower portion of the cartridge 10.

The blister chamber unit 12 may include a buffer chamber receiving a buffer. The buffer chamber is provided to receive pressure to feed the buffer. The blister chamber part 12 may be fluidly connected to the flow path of the base plate 100. The buffer, which is fed by receiving pressure, may be moved to the target chamber along the flow path of the base plate 100.

The blister chamber unit 12 may include a lysis buffer chamber 161 receiving a lysis buffer, a binding buffer chamber 162 receiving a binding buffer, first and second washing buffer chambers 163 and 164 receiving a washing buffer, and an elution buffer chamber 165 receiving an elution buffer.

The blister chamber unit 12 may be a blister plate 170 provided as a separate member from the base plate 100. Each blister chamber of the blister plate 170 may be fluidly connected to each of the buffer flow paths 131 and 132 of the base plate 100. In this case, the cover membrane may form a through hole for opening the portion where the buffer flow paths 131 and 132 of the base plate 100 and the outlet of the blister chamber are fluidly connected.

A plurality of blister chambers may be disposed side by side. For example, the binding buffer chamber 162 receiving the binding buffer, the first and second washing buffer chambers 163 and 164 receiving the washing buffer, the elution buffer chamber 165 receiving the elution buffer, and the lysis buffer chamber 161 receiving the lysis buffer may be disposed from the left.

The detection device includes a pressurizing means for pressurizing the blister chamber to feed the buffer solution thereinside to the buffer flow paths 131 and 132 of the base plate 100. For example, the pressurizing means may include various means, such as a cam structure, a piston structure, a lever structure, or a magnetic structure.

The blister chamber may include a first blister chamber 171 and a second blister chamber 172 that are spatially separated and connected through a fluid passage. For example, the second blister chamber 172 may have a larger volume than the first blister chamber 171. The first blister chamber 171 and the second blister chamber 172 may be connected through a blister connection passage 173. The first blister chamber 171 may be positioned on an upper side of the drawings, and the second blister chamber 172 may be positioned on a lower side of the drawings.

Figure 2:
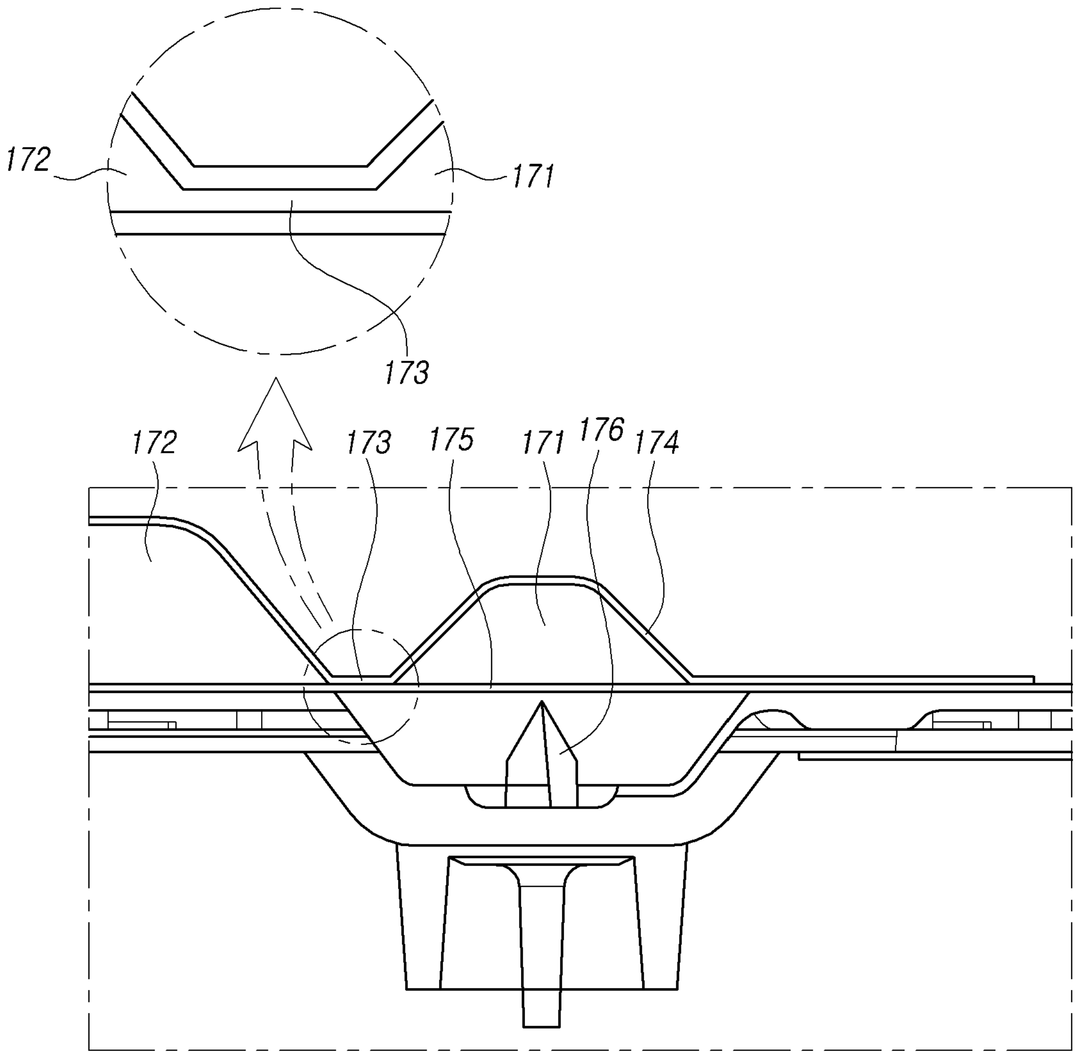
FIG. 2 is a cross-sectional view illustrating a blister chamber.

FIG. 2 is a cross-sectional view illustrating a blister chamber. The upper and lower directions are described with respect to the drawings of FIG. 2.

Referring to FIG. 2, the blister chamber may include a rupturable first blister membrane 174 and a second blister membrane 175 coupled to the first blister membrane 174 while forming a blister space capable of receiving a fluid. The first blister membrane 174 and the second blister membrane 175 may be bonded to each other by thermo-compression, an adhesive layer or an adhesive.

In the blister chambers 171 and 172, the second blister membrane 175 is broken by pressure and/or a sharp means (e.g., pin), and the first blister membrane 174 is compressed by the pressure, so that the fluid inside the blister chamber may flow out through the broken portion of the second blister membrane 175.

The first blister chamber 171 is pressurized while a first pressurizing means (not shown) of the detection device, positioned above, descends and, by the pressure of the first pressurizing means, the first blister membrane 174 is deformed. The second blister membrane 175 is deformed by the fluid pressure inside the first blister membrane 174. The second blister membrane 175 positioned under the first blister chamber 171 is ruptured while contacting the pin 176 positioned below.

Subsequently or simultaneously, the second blister chamber 172 is pressurized while a second pressurizing means (not shown) of the detection device, positioned thereabove, descends and, by the pressure of the second pressurizing means, the first blister membrane 174 is deformed to push out the fluid thereinside to the first blister chamber 171. The fluid received in the second blister chamber 172 flows to the first blister chamber 171 through the blister connection passage 173 and is fed to the buffer flow paths 131 and 132 of the base plate 100 through the ruptured portion of the second blister membrane 175 under the first blister chamber 171.

The first pressurizing means and/or the second pressurizing means maintains the state of pressurizing the first blister chamber 171 and/or the second blister chamber 172, preventing the fed fluid from returning to the inside of the blister chamber from the buffer flow paths 131 and 132.

The connection relationship between the chamber, the flow path, and the valve formed in the base 11 of the target analyte detection cartridge 10 is described below. Hereinafter, dividing the fluid paths is so done for convenience of description, and the functions are not limited by the denotations of the flow paths. The same flow path may be denoted by two or more terms.

Referring back to FIG. 1, the fluid path may be formed between the first pneumatic flow path 111 and the second pneumatic flow path 113. Each chamber communicates with one or more chambers through one or more flow paths and may include a valve for opening and closing each flow path. In other words, chambers and flow paths may be connected between the first pneumatic flow path 111 and the second pneumatic flow path 113 to form a plurality of fluid paths.

Hereinafter, the pneumatic flow paths 111 and 113 refer to flow paths in which a liquid fluid does not move but only a gas moves.

An internal control bead 151, a protease K bead 152, and a magnetic bead 153 may be provided in the fluid path. The internal control bead 151 and the protease K bead 152 may be provided in a freeze-dried state. The beads may be provided in a space formed in the flow path or may be provided inside the chamber.

The sample chamber 101 may provide a space for receiving the injected sample. For example, the sample may be injected through a pipette, or a container containing the sample may be inserted. The sample chamber 101 may be positioned in the upper right portion of the cartridge 10.

The sample chamber 101 may be provided so that the sample may be injected from one surface (front surface) of the base 11. Alternatively, the sample chamber 101 may be provided so that the sample may be injected from an edge (upper edge) of the base 11. The edge means 4 sides except for the 2 wide sides of the plate-shaped base 11.

The sample chamber 101 may include an injection space 101*a* into which the sample is injected and a liquid feeding space 101*b* connected to the injection space 101*a* to collect the injected sample and connected to the sample flow path 121. The injection space 101*a* may have an inlet through which the sample is injected. For stable sample injection, the inlet of the injection space 101*a* may have a larger area than the liquid feeding space 101*b*. The injection space 101*a* may be opened and closed by a closure. The closure may be integrally formed with the base 11 to prevent loss.

The closure may be provided on the front surface of the base 11. Accordingly, the inlet of the injection space 101*a* may be provided to have a larger area. Alternatively, the closure may be provided on the upper edge of the base 11.

According to an embodiment, the cartridge 10 may be inserted in an erected state with the wide side of the base 11 facing the front. In the state in which the cartridge 10 is inserted, the injection space 101*a* may be positioned above, and the liquid feeding space 101*b* may be positioned below. Accordingly, the sample injected into the injection space 101*a* may be moved to the liquid feeding space 101*b* by gravity.

The liquid feeding space 101*b* may be connected to the sample flow path 121 through an outlet positioned in the direction of gravity (downward in the drawings). The outlet of the liquid feeding space 101*b* or sample flow path 121 may be provided with a sample shutoff valve.

The sample shutoff valve is in a closed state in its initial state and be switched to an open state by an operation signal. This is because, if the sample is injected in the open state of the first valve 141, the sample may leak along the metering flow path 122.

For example, the sample shutoff valve may be a ball valve. In the initial state of the ball valve, a ball blocks the flow path and, if the plunger pressurizes the ball by an operation signal, the ball moves off to open the blocked flow path. The ball of the sample shutoff valve may be provided not to return to the initial position after moving off. For example, the ball may move off and drop downward by gravity.

The sample flow path 121 is connected to the metering flow path 122 through the first valve 141. The first valve 141 may open and close the sample flow path 121 or the metering flow path 122. The sample flow path 121 and the metering flow path 122 may be divided with respect to the first valve 141. In other words, the flow path between the first valve 141 and the sample chamber 101 may be referred to as the sample flow path 121, and the flow path between the first valve 141 and the metering chamber 102 may be referred to as the metering flow path 122.

The metering flow path 122 may include a flow path between the first valve 141 and the metering chamber 102, a flow path between the second valve 142 and the metering chamber 102, and a flow path between the metering chamber 102 and the waist flow path 125.

The metering chamber 102 may be used to meter a predetermined amount of sample or a quantity of sample. The metering chamber 102 may be positioned adjacent to the sample chamber 101 and may be positioned, e.g., on the left side of the sample chamber 101. The metering chamber 102 may be in the form of extending long in the upper/lower direction (or the direction of gravity).

The metering chamber 102 may be connected to the flow paths below and above in the direction of gravity. Accordingly, the metering chamber 102 may remove air bubbles present in the sample through the flow path above the metering chamber 102, thereby filling the inside of the metering chamber 102 with the sample and enabling quantitative metering.

A lower portion of the metering chamber 102 may be connected to the metering flow path 122, and an upper portion thereof may be connected to the first pneumatic flow path 111 or the first waste flow path 125. Specifically, the first pneumatic flow path 111 and the metering flow path 122 and the first waste flow path 125 may join at a point. The flow path connected to the first pneumatic port 112 at the joining point may be referred to as the first pneumatic flow path 111, the flow path connected to the metering chamber 102 at the joining point may be referred to as the metering flow path 122, and the flow path connected to the waste chamber 103 at the joining point may be referred to as the waste flow path 125. The metering flow path 122 above and below the metering chamber 102 may be a part of the metering chamber 102.

The inlet of the first pneumatic flow path 111 may be connected to the pneumatic means through the first pneumatic port 112. The first pneumatic flow path 111 may join the metering chamber 102 and be connected to the waste chamber 103 through the first waste flow path 125.

The waste chamber 103 may be positioned on the right side of the sample chamber 101 and be provided long in the upper/lower direction to secure a volume. The first waste flow path 125 may be connected to a side of an upper portion of the waste chamber 103, the second waste flow path 126 may be connected to another side of the upper portion, and the buffer drain flow path 127 may be connected to another side of the upper portion. The waste chamber 103 may be connected to the first pneumatic flow path 111 through the first waste flow path 125 and may be connected to the second pneumatic flow path 113 through the second waste flow path 126.

The second waste flow path 126 may be connected to the drain flow path 124 through the third valve 143. The drain flow path 124 may be connected to the mixing chamber 104. The mixing chamber 104 may be connected to the second pneumatic flow path 113. The second waste flow path 126 may be a part of the drain flow path 124.

Further, the inlet of the metering chamber 102 may be connected to the inlet of the mixing chamber 104 through the mixing flow path 123 connected to the metering flow path 122. A second valve 142 for opening and closing the mixing flow path 123 may be provided.

The outlet of the mixing chamber 104 may be connected to the waste chamber 103 through the drain flow path 124 and the second waste flow path 126. A third valve 143 for opening and closing the drain flow path 124 may be provided.

The internal control bead 151 (IC bead) may be provided in the mixing flow path 123 between the second valve 142 and the mixing chamber 104 as shown in the figure or may alternatively be provided inside the mixing chamber 104.

The magnetic bead 153 may be provided inside the mixing chamber 104. The magnetic bead 153 may be movable in response to an electromagnetic field of a magnetic means mounted in the target analyte detection device.

The magnetic means may be positioned close to one surface of the cartridge 10 and may be turned on/off by an electrical signal. Alternatively, the magnetic means may remain on during the processing operation of the cartridge 10 and, as its position relative to the mixing chamber 104 changes, adjust the transfer of the electromagnetic field.

The magnetic means and the ultrasonic means and the heating means described below may be disposed to be movable relative to each other. For example, the detection device may include an axially rotatable wheel structure, and a magnetic means, an ultrasonic means, and a heating means may be installed in the wheel structure. Accordingly, the magnetic means, the ultrasonic means, or the heating means may be positioned close to the mixing chamber 104 while the wheel structure is rotated.

The protease K bead 152 may be provided on the outlet side of the first buffer flow path 131 or be provided inside the mixing chamber 104.

The mixing chamber 104 may receive ultrasonic waves by an ultrasonic means (ultrasonic horn) mounted in the target analyte detection device. The ultrasonic means may generate ultrasonic waves while vibrating, promoting mixing of different fluids in the mixing chamber 104. The ultrasonic means may promote dissolution of the beads in the solution contained in the mixing chamber 104.

The mixing chamber 104 may include a heating element (e.g., Peltier element) to generate heat or may receive heat from the heating means mounted in the target analyte detection device. The heating means may generate heat and transfer it to the mixing chamber 104 to increase the temperature inside the mixing chamber 104, promoting the mixing reaction, dissolution reaction, or chemical reaction.

The mixing chamber 104 may be divided into an upper space and a lower space. The upper space and the lower space may be spatially separated while being connected to each other.

The upper space of the mixing chamber 104 may be provided with an inlet through which a fluid is introduced and have the internal control bead 151 (IC bead) and the protease K bead 152. The magnetic bead 153 may be provided in the lower space of the mixing chamber 104 and may be provided as a space in which the sample and the buffer or reagent are mixed. The drain flow path 124 may be connected to the lower space of the mixing chamber 104.

It is possible to prevent the mixed solution from splashing into the upper space while mixing in the lower space of the mixing chamber 104. For example, a blocking wall may be provided in a portion except for the passage between the upper space and the lower space of the mixing chamber 104.

The mixing chamber 104 may be connected to the lysis buffer chamber 161, the binding buffer chamber 162, the first and second washing buffer chambers 163 and 164, and the elution buffer chamber 165 through the buffer flow paths 131 and 132.

The first buffer flow path 131 may fluidly connect the lysis buffer chamber 161 to the mixing chamber 104.

The second buffer flow path 132 may fluidly connect the binding buffer chamber 162, the first washing buffer chamber 163 and the second washing buffer chamber 164, and the elution buffer chamber 165 to the mixing chamber 104. The second buffer flow path 132 may be branched between the mixing chamber 104 and the fifth valve 145, and the branch flow paths may be connected to four different buffer chambers 162, 163, 164, and 165, respectively.

One end of the second buffer flow path 132 may be connected to the mixing chamber 104, and the other end thereof may be connected to the buffer drain flow path 127 connected to the waste chamber 103. The second buffer flow path 132 and the buffer drain flow path 127 may be connected through the fifth valve 145. The buffer drain flow path 127 may be a part of the second buffer flow path 132.

The mixing chamber 104 may be connected to the detection chamber 105 through the detection flow path 133. A fourth valve 144 for opening and closing the detection flow path 133 may be provided.

One end of the detection flow path 133 may be connected to the mixing chamber 104, and the other end thereof may be connected to each of the plurality of detection chambers 105. The detection flow path 133 may be opened and closed by the fourth valve 144. The detection flow path 133 may be branched into a plurality of branch flow paths corresponding to the plurality of detection chambers 105 at the fourth valve 144 or at the rear end of the fourth valve 144. For example, the detection flow path 133 may be branched into six branch flow paths respectively connected to the six detection chambers 105.

The fourth valve 144 may further include an air collecting space. Air bubbles generated during the mixing process in the mixing chamber 104 may move to the air collection space provided above the fourth valve 144 so that the sample fluid free from air bubbles may be moved through the detection flow path 133.

The plurality of detection chambers 105 may be positioned side by side along the upper and lower directions on the left edge of the base 11. For example, the plurality of detection chambers 105 may be provided close to an end portion where the cartridge 10 is inserted into the detection device. The target analyte detection device may be provided with a detection module capable of inspecting whether the target analyte is present in the detection chambers 105 provided in the inserted cartridge 10. For example, the detection module may include an LED that emits excitation light and a photodiode that receives reflected light reflected from the detection chamber 105.

The detection chamber 105 may include a detection reagent therein. The detection reagent may be prepared in a freeze-dried state. If the sample fluid flows into the detection chamber 105 through the detection flow path 133, a detection reaction may occur as the detection reagent is dissolved.

The target analyte detection device may include a detection chamber heating means for transferring heat to the detection chamber 105. If heat is transferred from the detection chamber heating means, the temperature of the detection chamber 105 is increased to and maintained at a certain temperature so that a detection reaction may occur inside the detection chamber 105.

Each detection chamber 105 may be connected to the detection buffer chamber 106. The detection buffer chamber 106 may be a space for receiving the sample fluid overflowing the detection chamber 105, a space for storing the air of the detection flow path 133 and the detection chamber 105, or a space for storing the gas generated in the detection chamber 105.

The six detection buffer chambers 106 may all have the same volume. As the air is pushed out while the sample fluid moves through the detection flow path 133 and the detection chamber 105 and is stored in each buffer chamber 106, the six detection buffer chambers 106 all may provide the same reaction force. Accordingly, the same amount of sample fluid may be provided to each detection chamber 105.

A process for detecting a target analyte using the cartridge 10 according to an embodiment is described below.

A robot of the target analyte detection device may wait for a user input to execute the protocol.

Sample Loading and Cartridge Mounting

The user may load the sample into the injection space 101*a* of the sample chamber 101. For example, after opening the closure and injecting the sample into the injection space 101*a* through a pipette, the user may close and seal the closure.

The user may seat or insert and mount the cartridge 10 into the insertion portion of the target analyte detection device and then input an operation signal for starting the detection process through the control panel of the detection device. Alternatively, after recognizing the mounting or insertion of the cartridge 10 in the insertion portion, the detection device may perform the protocol after a predetermined time elapses without the user's operation signal.

The robot performs the following protocol.

If the mounting of the cartridge 10 is recognized, the robot arm where the cartridge 10 is mounted clamps the cartridge 10. The robot arm moves the cartridge 10 to the operation position. The operating position of the cartridge 10 may be the same as the detection position. For example, if the cartridge 10 is moved to the operation position, the detection chamber 105 may be positioned below the detection module.

In the initial state before the process of the cartridge 10 is started, all the valves 141 to 145 and the air injection flow paths 111 and 113 may be in the open state. However, the sample shutoff valve provided at the outlet or the rear end of the outlet of the liquid feeding space 101*b* may be in the closed state in the initial state. The pressurizing module that applies pressure to the blister chamber may also be in the initial state (open state).

Sample Metering Process

Figure 3:
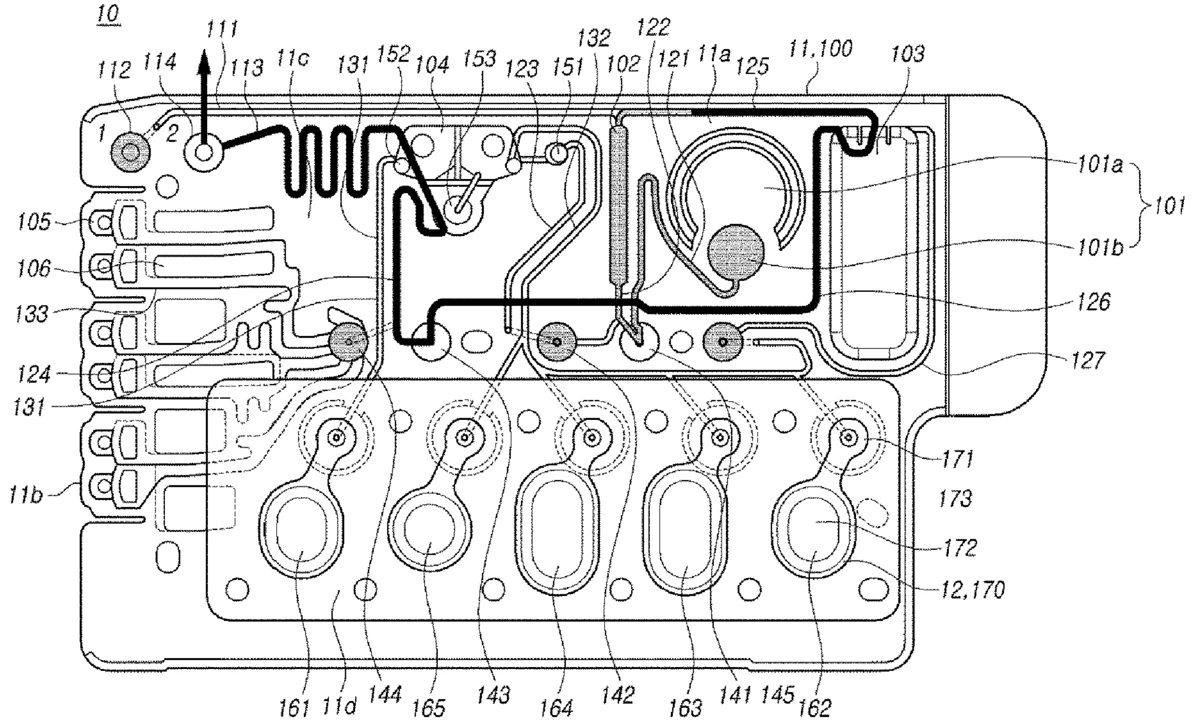
FIGS. 3, 4 and 5 are views illustrating a sample metering process.
Figure 4:
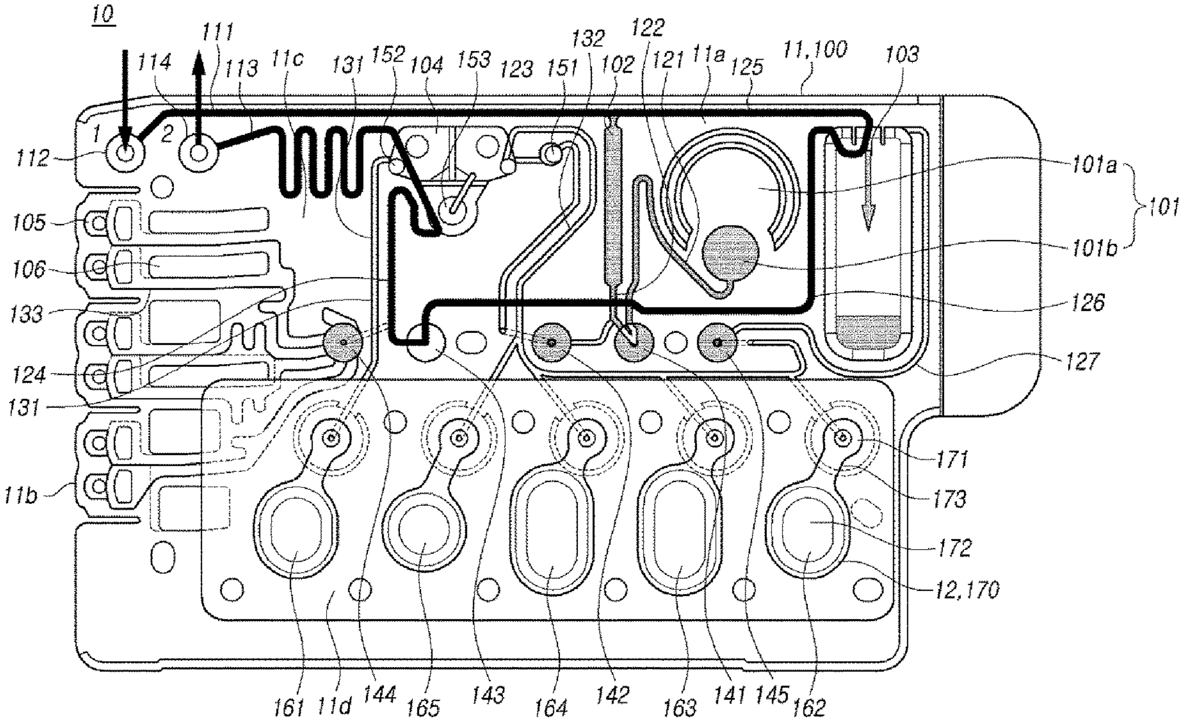
Figure 5:
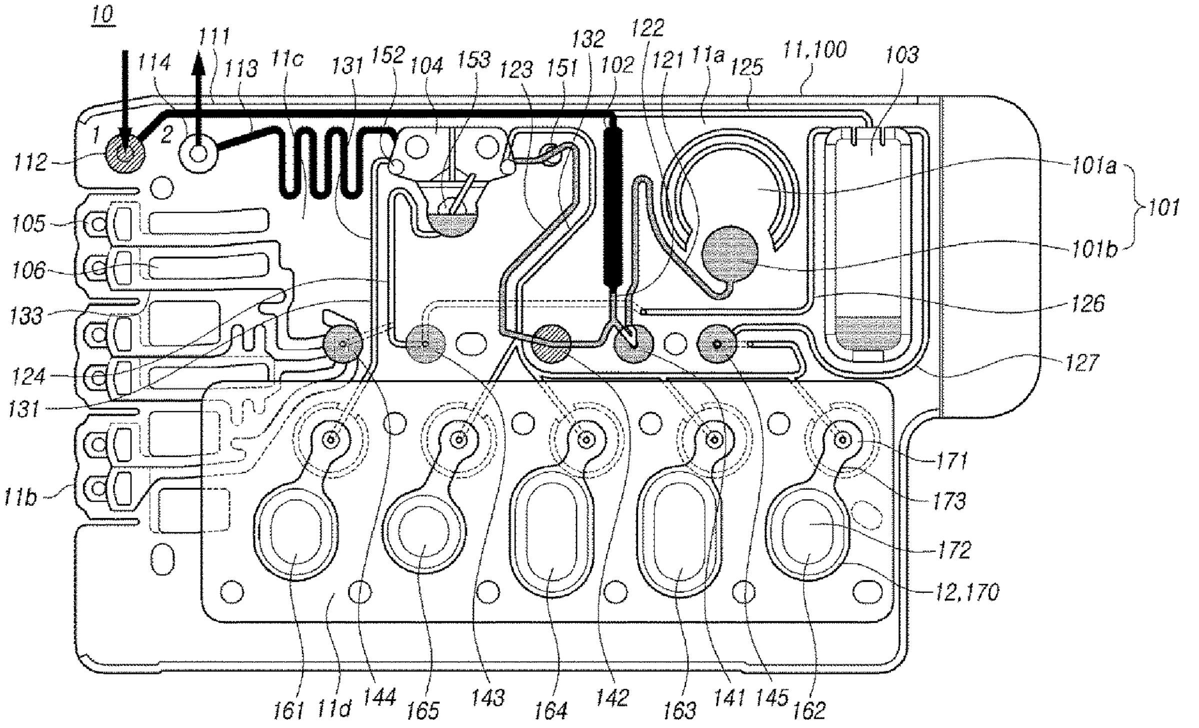

FIGS. 3 to 5 are views illustrating a sample metering process.

Then, the detection device may perform a metering process of metering a predetermined amount of sample or a quantity of sample in the sample chamber 101.

Referring to FIG. 3, the valve controller may open the first valve 141 and the third valve 143 while closing the remaining valves. The valve controller may open the sample shutoff valve provided at the outlet of the liquid feeding space 101*b* to flow the sample to the sample flow path 121.

The pneumatic controller closes the first pneumatic port 112 and opens the second pneumatic port 114 and may then provide negative pressure through the second pneumatic port 114. The provided negative pressure may be in turn transferred to the second pneumatic flow path 113, the mixing chamber 104, the drain flow path 124, the third valve 143, the second waste flow path 126, the waste chamber 103, the first waste flow path 125, the metering chamber 102, the metering flow path 122, the sample flow path 121, and the sample chamber 101.

Thereafter, the sample in the sample chamber 101 fills the metering flow path 122 and the metering chamber 102, overflows the metering chamber 102, and then moves until filling a portion of the first waste flow path 125 or may reach through the first waste flow path 125 to the waste chamber 103.

Then, referring to FIG. 4, the valve controller may switch the first valve 141 to the closed state. The pneumatic controller opens the first pneumatic port 112 and the second pneumatic port 114 and may then provide positive pressure through the first pneumatic port 112 or negative pressure through the second pneumatic port 114.

The provided positive pressure may be in turn transferred to the first pneumatic flow path 111, the first waste flow path 125, the waste chamber 103, the second waste flow path 126, the third valve 143, the drain flow path 124, the mixing chamber 104, and the second pneumatic flow path 113.

In this process, the sample remaining in the first waste flow path 125 is discarded to the waste chamber 103. As the sample overflowing the metering chamber 102 is discarded into the waste chamber 103, the volume of the sample filling the metering chamber 102 from the first valve 141 may be metered. The process of blowing air to remove the overflowed sample may be referred to as an air knife process.

Then, referring to FIG. 5, the process of transferring the metered sample to the mixing chamber 104 may proceed.

The valve controller may switch the second valve 142 to the open state and may switch the third valve 143 to the closed state. The pneumatic controller may provide positive pressure through the first pneumatic port 112 or negative pressure through the second pneumatic port 114.

The provided positive pressure may be in turn transferred to the first pneumatic flow path 111, the metering chamber 102, the metering flow path 122, the second valve 142, the mixing flow path 123, and the mixing chamber 104. In this process, the sample filling the metering chamber 102 may be transferred to the mixing chamber 104 through the second valve 142 and the mixing flow path 123.

The internal control bead 151 positioned in the mixing flow path 123 may be dissolved in the sample passing through the mixing flow path 123 and be transferred to the mixing chamber 104. Or, if the internal control bead 151 is positioned in the mixing chamber 104, the internal control bead 151 may be dissolved by the sample transferred to the mixing chamber 104.

Lysis Process

Next, the lysis buffer is transferred to the mixing chamber 104, and the lysis process may be performed in the mixing chamber 104.

The valve controller may switch the second valve 142 to the closed state to close all the valves. The pneumatic controller may close the first pneumatic port 112 and provide negative pressure through the second pneumatic port 114. The provided negative pressure may in turn be transferred to the second pneumatic flow path 113 and the first buffer flow path 131.

The blister pressurizing means may simultaneously pressurize the lysis buffer chamber 161 to supply the lysis buffer. In this process, the lysis buffer of the lysis buffer chamber 161 is transferred to the mixing flow path 123 through the first buffer flow path 131. The protease K bead 152 positioned on the outlet side of the first buffer flow path 131 may be dissolved in the lysis buffer and transferred to the mixing chamber 104.

The ultrasonic means generates ultrasonic waves in the mixing chamber 104 to mix the sample and the lysis buffer. The heating means applies heat to the mixing chamber 104 and incubates for a predetermined time.

Binding Process

Next, the binding buffer is transferred to the mixing chamber 104, and the binding process may be performed in the mixing chamber 104.

The pneumatic controller may provide negative pressure through the second pneumatic port 114. The provided negative pressure may in turn be transferred to the second pneumatic flow path 113, the mixing chamber 104, and the second buffer flow path 132.

The blister pressurizing means may simultaneously pressurize the binding buffer chamber 162 to supply the binding buffer. In this process, the binding buffer of the binding buffer chamber 162 is transferred to the mixing flow path 123 through the second buffer flow path 132.

Then, the valve controller may switch the fifth valve 145 to the open state to open the second waste flow path 126. The pneumatic controller may provide positive pressure through the first pneumatic port 112. The provided positive pressure may in turn be transferred to the first pneumatic flow path 111, the first waste flow path 125, the waste chamber 103, the buffer drain flow path 127, the fifth valve 145, the second buffer flow path 132, the mixing chamber 104, and the second pneumatic flow path 113. In this process, the binding buffer remaining in the second buffer flow path 132 may be completely discharged to the mixing chamber 104.

Then, the valve controller may switch the fifth valve 145 to the closed state to close all the valves. The pneumatic controller may close both the first pneumatic port 112 and the second pneumatic port 114.

The ultrasonic means generates ultrasonic waves in the mixing chamber 104 to mix the sample and the binding buffer. After a certain time elapses and the binding process is completed, the magnetic means generates an electromagnetic field to collect the magnetic beads 153.

Then, a drain process of the mixing chamber 104 may be performed. The valve controller may switch the third valve 143 to the open state to open the drain flow path 124. The pneumatic controller may provide negative pressure through the first pneumatic port 112 or positive pressure through the second pneumatic port 114. In this process, the solution in the mixing chamber 104 is dumped into the waste chamber 103 through the drain flow path 124. In this case, the magnetic bead 153 remains attached to the magnetic means.

First Washing Process

Then, a first washing buffer is transferred to the mixing chamber 104, and a first magnetic bead washing process may proceed.

The pneumatic controller may shut off the first pneumatic port 112 and provide negative pressure through the second pneumatic port 114. The valve controller may switch the third valve 143 to the closed state to close all the valves.

The blister pressurizing means may simultaneously pressurize the first washing buffer chamber 163 to supply the washing buffer. In this process, the first washing buffer of the first washing buffer chamber 163 is transferred to the mixing chamber 104 through the second buffer flow path 132.

The pneumatic controller may provide positive pressure through the first pneumatic port 112. The valve controller may switch the fifth valve 145 to the open state to open the buffer drain flow path 127. In this process, the first washing buffer remaining in the second buffer flow path 132 is transferred into the mixing chamber 104, emptying the second buffer flow path 132.

The magnetic means stops the operation, and the magnetic bead 153 attached to the magnetic means is detached in the mixing chamber 104. The ultrasonic means generates ultrasonic waves in the mixing chamber 104 to mix the magnetic beads 153 and the first washing buffer. The heating means applies heat to the mixing chamber 104 and incubates for a predetermined time. After a certain time elapses and the first washing process is completed, the magnetic means generates an electromagnetic field to collect the magnetic beads 153.

Then, a drain process of the mixing chamber 104 may be performed. The valve controller may switch the third valve 143 to the open state to open the drain flow path 124. The pneumatic controller may provide negative pressure through the first pneumatic port 112 or positive pressure through the second pneumatic port 114.

In this process, the solution in the mixing chamber 104 is dumped into the waste chamber 103 through the drain flow path 124. In this case, the magnetic bead 153 remains attached to the magnetic means.

Second Washing Process

Then, a second washing buffer is transferred to the mixing chamber 104, and a second magnetic bead washing process may proceed.

The pneumatic controller may shut off the first pneumatic port 112 and provide negative pressure through the second pneumatic port 114. The valve controller may switch the third valve 143 to the closed state to close all the valves.

The blister pressurizing module may simultaneously pressurize the second washing buffer chamber 164 to supply the washing buffer. In this process, the second washing buffer of the second washing buffer chamber 164 is transferred to the mixing chamber 104 through the second buffer flow path 132.

The pneumatic controller may provide positive pressure through the first pneumatic port 112. The valve controller may switch the fifth valve 145 to the open state to open the buffer drain flow path 127. In this process, the second washing buffer remaining in the second buffer flow path 132 is transferred into the mixing chamber 104, emptying the second buffer flow path 132.

The magnetic means stops the operation, and the magnetic bead 153 attached to the magnetic means is detached in the mixing chamber 104. The ultrasonic means generates ultrasonic waves in the mixing chamber 104 to mix the magnetic beads 153 and the second washing buffer. The heating means applies heat to the mixing chamber 104 and incubates for a predetermined time. After a certain time elapses and the second washing process is completed, the magnetic means of the detection device is operated to collect the magnetic beads 153.

Then, a drain process of the mixing chamber 104 may be performed. The valve controller may switch the third valve 143 to the open state to open the drain flow path 124. The pneumatic controller may provide negative pressure through the first pneumatic port 112 or positive pressure through the second pneumatic port 114.

In this process, the solution in the mixing chamber 104 is dumped into the waste chamber 103 through the drain flow path 124. In this case, the magnetic bead 153 remains attached to the magnetic means.

All or some steps of the second magnetic bead washing process described above may be omitted depending on circumstances.

Heating and Incubating Process

Then, the heating and incubating process of the mixing chamber 104 may proceed.

The heating means applies heat to the mixing chamber 104 and incubates for a predetermined time.

The valve controller may block the first pneumatic port 112 and provide negative pressure through the second pneumatic port 114 to remove the evaporated residual washing buffer.

Elution Process

Then, an elution process of the mixing chamber 104 may be performed.

The pneumatic controller may shut off the first pneumatic port 112 and provide negative pressure through the second pneumatic port 114. The valve controller may maintain all the valves in the closed state.

The blister pressurizing means may simultaneously pressurize the elution buffer chamber 165 to supply the elution buffer. In this process, the elution buffer of the elution buffer chamber 165 is transferred to the mixing chamber 104 through the second buffer flow path 132.

The pneumatic controller blocks the first pneumatic port 112 and provides negative pressure through the second pneumatic port 114 to vent the evaporated gas in the mixing chamber 104.

Then, the pneumatic controller may provide positive pressure through the first pneumatic port 112. The valve controller may switch the fifth valve 145 to the open state to open the buffer drain flow path 127. In this process, the elution buffer remaining in the second buffer flow path 132 is transferred into the mixing chamber 104, emptying the second buffer flow path 132.

The ultrasonic means generates ultrasonic waves in the mixing chamber 104 to mix the magnetic beads 153 and the elution buffer. The heating means applies heat to the mixing chamber 104 and incubates for a predetermined time. After a certain time elapses and the elution process is completed, the magnetic means generates an electric field to collect the magnetic beads 153.

Detection Process

Next, a pre-detection process of transferring the elution buffer mixed with the reaction sample in the mixing chamber 104 to the detection chamber 105 may be performed.

The valve controller may switch the fourth valve 144 to the open state to open the detection flow path 133. The pneumatic controller may block the first pneumatic port 112 and provide positive pressure through the second pneumatic port 114. In this process, the reaction sample mixed with the elution buffer in the mixing chamber 104 is transferred into the detection chamber 105.

Then, a detection reaction may occur in the detection chamber 105 and a detection process may proceed.

The valve controller may switch the fourth valve 144 to the closed state to close all the valves. The solution transferred from the mixing chamber 104 to the detection chamber 105 through the detection flow path 133 may dissolve the detection beads in the detection chamber 105.

The detection chamber heating means may apply heat to the detection chamber 105 to perform a PCR reaction for a predetermined time. The PCR reaction may be performed at a predetermined temperature for a predetermined time, and a plurality of reactions may proceed at two or more temperatures.

The pressure increased while the detection chamber 105 is heated may be released through the detection buffer chamber 106. For example, the gas generated in the detection chamber 105 may move to the detection buffer chamber 106.

The same amount of reaction solution should be transferred to the plurality of detection chambers 105. To that end, the branch detection flow paths 133 branched from the fourth valve 144 may have the same length. This is why the flow rate of the liquid flowing through the flow path is inversely proportional to the drag coefficient of the flow path, and the resistance coefficient is proportional to the length of the flow path. For example, the branch detection flow path 133 connected to the detection chamber 105 close to the fourth valve 144 may include a plurality of bends to increase the length of the flow path. The branch detection flow path 133 connected to the detection chamber 105 far away from the fourth valve 144 may be provided as the shortest path to shorten the length.

Alternatively, the branch detection flow paths 133 branched from the fourth valve 144 may have different inlet areas. For example, the branch detection flow path 133 connected to the detection chamber 105 close to the fourth valve 144 may have a relatively small inlet area. The branch detection flow path 133 connected to the detection chamber 105 far away from the fourth valve 144 may have a relatively large inner diameter. This is why the flow rate of the liquid flowing through the flow path is inversely proportional to the drag coefficient of the flow path, and the resistance coefficient is inversely proportional to the cross-sectional area of the flow path.

Or, even when the lengths or inlet areas of the branch detection flow paths 133 do not differ, the same flow rate may be transferred to each branch detection flow path 133 by the pressure of the detection buffer chamber 106 after a sufficient time elapses. In other words, in the initial stage when the fluid is transferred to the detection flow path 133, a different flow rate may be transferred to each detection chamber 105, but the detection chamber 105, which is filled with the fluid at a relatively short time, has a large pressure applied thereto, as compared with the detection chamber 105 not yet filled with the fluid. Accordingly, after a predetermined time elapses, pressure equilibrium may occur in all the detection flow paths 133 and the detection chambers 105, so that the same amount of fluid fills each detection chamber 105.

Then, if the detection reaction is completed, the detection module detects the target analyte in the detection chamber 105. For example, the detection module may generate detection light and emit the detection light to the detection chamber 105 and receive reflected light reflected from the target analyte to inspect the target analyte.

Finally, before the cartridge 10 on which the detection process is completed is removed from the detection device, a process of releasing the pressure of the cartridge 10 may be performed. The pneumatic controller provides negative pressure through the second pneumatic port 114, and the valve controller switches the fourth valve 144 to the open state to open the detection flow path 133.

In this process, the gas of the detection chamber 105 and the detection flow path 133 is vented to the second pneumatic port 114.

Cartridge Removal

After all the reactions are finished, the valve controller switches all the valves to the open state, and the pneumatic controller opens the first and second pneumatic ports 112 and 114.

The cartridge 10 may be removed from the detection device.

Figure 6:
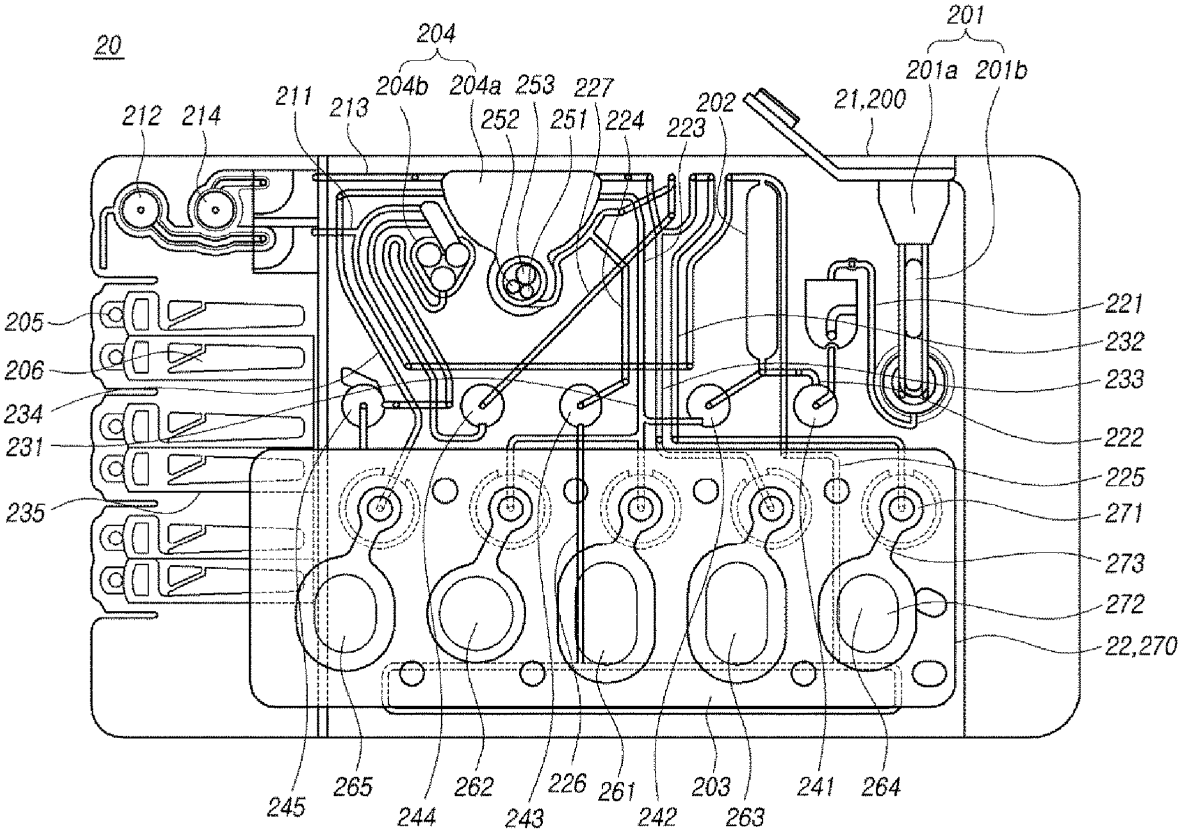
FIG. 6 is a plan view illustrating a cartridge according to another embodiment of the disclosure.

FIG. 6 is a plan view illustrating a cartridge 20 according to another embodiment of the disclosure.

Referring to FIG. 6, a cartridge 20 of a target analyte detection device according to another embodiment of the disclosure may include a base 21 having a plurality of chambers and flow paths, a cover (transparent) sealing one or two opposite surfaces of the base 21, and a blister chamber unit 22 fluidly coupled to the base 21 to provide a buffer.

The blister chamber unit 22 may be provided as a member separate from the base 21 and fluidly connected thereto, and be coupled to one surface of the base 21 through, e.g., an adhesive. An embodiment in which the blister chamber unit 22 is provided as a separate member from the base 21 is described below.

The base 21 may include a sample chamber 201 into which sample is inserted or for receiving a sample, a metering chamber 202 for metering a predetermined amount of sample or a quantity of sample, a waste chamber 203 for storing the wasted fluid, a first mixing chamber 204*a* for mixing the sample with a reagent, a second mixing chamber 204*b* where an elution reaction occurs, and a detection chamber 205 where a sample detection reaction (e.g., PCR reaction) and target analyte detection occur.

The base 21 may form flow paths for connecting the chambers and may include valves for opening and closing the flow paths.

The base 21 may be a plate-shaped base plate 200. A chamber, flow path, and valve may be formed on one surface of the base plate 200, and a flow path crossing the flow path formed on the one surface may be formed on another surface. Any flow paths may be provided on both the two opposite surfaces of the base plate 200 and be connected to each other through the base plate 200.

The base 21 may be provided to move in one direction (left direction in the drawings) to be mounted with respect to the target analyte detection device (not shown). For example, a rack is formed on a side edge (upper portion in the drawings) of the base 21, and the rack of the base 21 may be mechanically coupled with the pinion of the driving module provided in the target analyte detection device so that as the pinion rotates, the base 21 may move in one direction (left direction in the drawings). The base 21 may slide in one direction by use of various mechanical structures, e.g., a piston structure, as well as the rack-pinion structure, and may not only slide but also pivot, rotate, or swing.

The cover may be coupled to one surface of the base 21 to seal any one or more of the chamber, flow path, and valve formed on one surface (front surface in the drawings) of the base 21. The cover may include a first cover to seal one surface (front surface in the drawings) of the base 21 and a second cover to seal the other surface (back surface in the drawings) of the base 21.

According to another embodiment, the target analyte cartridge 20 may provide an air pressure to the flow path, moving the fluid. The base plate 200 may include a pneumatic flow path communicating with the fluid flow path. The pneumatic flow path may be connected to a pneumatic means for providing positive or negative pressure. As an example, the pneumatic means includes a pump.

The pneumatic flow path may include a first pneumatic flow path 211 and a second pneumatic flow path 213. Further, the first and second pneumatic flow paths 211 and 213 may be selectively used as air injection flow paths or as air discharge flow paths. For example, the first and second pneumatic flow paths 211 and 213 may be connected to the pump through a direction switching means, such as a solenoid valve.

When the solenoid valve is in a first position, the first pneumatic flow path 211 may be used as an air injection flow path, and the second pneumatic flow path 213 may be used as an air discharge flow path. Conversely, when the solenoid valve is in a second position, the first pneumatic flow path 211 may be used as an air discharge flow path, and the second pneumatic flow path 213 may be used as an air injection flow path. As such, the direction of the fluid flow may be adjusted by switching the direction of the pressure provided to the first pneumatic flow path 211 and the second pneumatic flow path 213.

The cover membrane may include pneumatic ports 212 and 214 for opening the pneumatic flow paths. The pneumatic ports 212 and 214 may include a first pneumatic port 212 connected to the first pneumatic flow path 211 and a second pneumatic port 214 connected to the second pneumatic flow path 213.

The meaning of opening or closing the pneumatic ports 212 and 214 may include the meaning of operating or stopping the pneumatic means connected to the pneumatic ports 212 and 214. The meaning of providing pneumatic pressure to the pneumatic ports 212 and 214 may include the meaning of operating the pneumatic means connected to the pneumatic ports 212 and 214 to transfer the pneumatic pressure to the pneumatic flow paths 211 and 213.

The blister chamber unit 22 may include a buffer chamber receiving a buffer. The buffer chamber is provided to receive pressure to feed the buffer. The blister chamber part 22 may be fluidly connected to the flow path of the base plate 200. The buffer, which is fed by receiving pressure, may be moved to the target chamber along the flow path of the base plate 200.

The blister chamber unit 22 may include a lysis buffer chamber 261 receiving a lysis buffer, a binding buffer chamber 262 receiving a binding buffer, first and second washing buffer chambers 263 and 264 receiving a washing buffer, and an elution buffer chamber 265 receiving an elution buffer.

The blister chamber unit 22 may be a blister plate 270 provided as a separate member from the base plate 200. Each blister chamber of the blister plate 270 may be fluidly connected to each of the buffer flow paths 231, 232, 233, and 234 of the base plate 200. In this case, the cover membrane may form a through hole for opening the portion where the buffer flow paths 231, 232, 233, and 234 of the base plate 200 and the blister chamber are fluidly connected.

In the blister chamber, a plurality of blister chambers may be disposed side by side. For example, a second washing buffer chamber 264 and first washing buffer chamber 263 for receiving a washing buffer, a lysis buffer chamber 261 for receiving a lysis buffer, a binding buffer chamber 262 for receiving a binding buffer, and an elution buffer chamber 265 for receiving an elution buffer may be disposed from the left.

The connection relationship between the chamber, the flow path, and the valve formed in the base 21 of the target analyte detection cartridge 20 is described below. Hereinafter, dividing the fluid paths is so done for convenience of description, and the functions are not limited by the denotations of the flow paths. The same flow path may be denoted by two or more terms.

The fluid path may be formed between the first pneumatic flow path 211 and the second pneumatic flow path 213. Each chamber communicates with one or more chambers through one or more flow paths and may include a valve for opening and closing each flow path. In other words, chambers and flow paths may be connected between the first pneumatic flow path 211 and the second pneumatic flow path 213 to form a plurality of fluid paths.

Hereinafter, the pneumatic flow paths 211 and 213 refer to flow paths in which a liquid fluid does not move but only a gas moves.

An internal control bead 251, a protease K bead 252, and a magnetic bead 253 may be provided in the fluid path. The internal control bead 251 and the protease K bead 252 may be provided in a freeze-dried state. The beads may be provided in a space formed in the flow path or may be provided inside the chamber.

The sample chamber 201 may provide a space for receiving the injected sample. For example, the sample may be injected through a pipette, or a container containing the sample may be inserted. The sample chamber 201 may be positioned in the upper right portion of the cartridge 20.

The sample chamber 201 may be provided so that the sample may be injected from an edge (upper edge) of the base 21. The edge means 4 sides except for the 2 wide sides of the plate-shaped base 21.

The sample chamber 201 may include an injection space 201*a* into which the sample is injected and a liquid feeding space 201*b* connected to the injection space 201*a* to collect the injected sample and connected to the sample flow path 221. The injection space 201*a* may have an inlet through which the sample is injected. For stable sample injection, the inlet of the injection space 201*a* may have a larger area than the liquid feeding space 201*b*. The injection space 201*a* may be opened and closed by a closure. The closure may be integrally formed with the base 21 to prevent loss.

According to an embodiment, the cartridge 20 may be inserted in an erected state with the wide side of the base 21 facing the front. In the state in which the cartridge 20 is inserted, the injection space 201*a* may be positioned above, and the liquid feeding space 201*b* may be positioned below. Accordingly, the sample injected into the injection space 201*a* may be moved to the liquid feeding space 201*b* by gravity.

The injection space 201*a* may have an inlet through which the sample is injected. For stable sample injection, the inlet of the injection space 201*a* may have a larger area than the liquid feeding space 201*b*. The liquid feeding space 201*b* may be in the form of a tube extending in the direction of gravity (downward in the drawings) of the cartridge 20.

The sample chamber 201 is positioned in the upper right portion of the cartridge 20, and the closure is positioned on the upper right edge of the cartridge 20. The injection space 201*a* may be opened and closed by a closure. The closure may be integrally formed with the base 21 to prevent loss. A rack used for entry and exit of the cartridge 20 may be formed on the left side of the closure.

The liquid feeding space 201*b* may be connected to the sample flow path 221 through an outlet positioned in the direction of gravity (downward in the drawings). The outlet of the liquid feeding space 201*b* or sample flow path 221 may be provided with a sample shutoff valve 246.

The sample shutoff valve 246 is in a closed state in its initial state and be switched to an open state by an operation signal. This is because, if the sample is injected in the open state of the first valve 241, the sample may leak along the metering flow path 222.

For example, the sample shutoff valve 246 may be a ball valve. In the initial state of the ball valve, a ball blocks the flow path and, if the plunger pressurizes the ball by an operation signal, the ball moves off to open the blocked flow path. The ball of the sample shutoff valve 246 may be provided not to return to the initial position after moving off. For example, the ball may move off and drop downward by gravity.

The sample flow path 221 is connected to the metering flow path 222 through the first valve 241. The first valve 241 may open and close the sample flow path 221 or the metering flow path 222. The sample flow path 221 and the metering flow path 222 may be divided with respect to the first valve 241. In other words, the flow path between the first valve 241 and the sample chamber 201 may be referred to as the sample flow path 221, and the flow path between the first valve 241 and the metering chamber 202 may be referred to as the metering flow path 222.

The metering flow path 222 may include a flow path between the first valve 241 and the metering chamber 202, a flow path between the second valve 242 and the metering chamber 202, and a flow path between the metering chamber 202 and the waist flow path 225.

The metering chamber 202 may be used to meter a predetermined amount of sample or a quantity of sample. The metering chamber 202 may be positioned adjacent to the sample chamber 201 and may be positioned, e.g., on the left side of the sample chamber 201. The metering chamber 202 may be in the form of extending long in the upper/lower direction (or the direction of gravity).

The metering chamber 202 may be connected to the flow paths below and above in the direction of gravity. Accordingly, the metering chamber 202 may remove air bubbles present in the sample through the flow path above the metering chamber 202, thereby filling the inside of the metering chamber 202 with the sample and enabling quantitative metering.

A lower portion of the metering chamber 202 may be connected to the metering flow path 222, and an upper portion thereof may be connected to the first pneumatic flow path 211 or the first waste flow path 225. Specifically, the first pneumatic flow path 211 and the metering flow path 222 and the first waste flow path 225 may join at a point. The flow path connected to the first pneumatic port 212 at the joining point may be referred to as the first pneumatic flow path 211, the flow path connected to the metering chamber 202 at the joining point may be referred to as the metering flow path 222, and the flow path connected to the waste chamber 203 at the joining point may be referred to as the waste flow path 225. The metering flow path 222 above and below the metering chamber 202 may be a part of the metering chamber 202.

The inlet of the first pneumatic flow path 211 may be connected to the pneumatic means through the first pneumatic port 212. The first pneumatic flow path 211 may join the metering chamber 202 and be connected to the waste chamber 203 through the first waste flow path 225.

The waste chamber 203 may be positioned under the blister chamber unit 22 and be provided long in the left/right direction to secure a volume. The first waste flow path 225 may be connected to a side of an upper portion of the waste chamber 203, and the second waste flow path 226 may be connected to another side of the upper portion. The waste chamber 203 may be connected to the first pneumatic flow path 211 through the first waste flow path 225 and may be connected to the second pneumatic flow path 213 through the second waste flow path 226.

The second waste flow path 226 may be connected to the drain flow path 224 through the third valve 243. The drain flow path 224 may be connected to the first mixing chamber

204*a*, and the first mixing chamber 204*a* may be connected to the second pneumatic flow path 213. The second waste flow path 226 may be a part of the drain flow path 224.

Further, the inlet of the metering chamber 202 may be connected to the inlet of the first mixing chamber 204*a* through the mixing flow path 223 connected to the metering flow path 222. A second valve 242 for opening and closing the mixing flow path 223 may be provided.

The outlet of the first mixing chamber 204*a* may be connected to the waste chamber 203 through the second waste flow path 226 connected to the drain flow path 224. A third valve 243 for opening and closing the drain flow path 224 may be provided.

The internal control bead 252 (IC bead) and the magnetic bead 253 may be provided inside the first mixing chamber 204*a*. The magnetic bead 253 may be movable in response to an electromagnetic field of a magnetic means mounted in the target analyte detection device.

The magnetic means may be positioned close to one surface of the cartridge 20 and may be turned on/off by an electrical signal. Alternatively, the magnetic means may remain on during the processing operation of the cartridge 20 and, as its position relative to the mixing chamber 104 changes, adjust the transfer of the electromagnetic field.

The magnetic means and the ultrasonic means and the heating means described below may be disposed to be movable relative to each other. For example, the detection device may include an axially rotatable wheel structure, and a magnetic means, an ultrasonic means, and a heating means may be installed in the wheel structure. Accordingly, the magnetic means, the ultrasonic means, or the heating means may be positioned close to the first mixing chamber 204*a* while the wheel structure is rotated.

The protease K beads 252 may be provided inside the second mixing chamber 204*b*.

The first mixing chamber 204*a* or the second mixing chamber 204*b* may receive ultrasonic waves by an ultrasonic means (ultrasonic horn) mounted in the target analyte detection device. The ultrasonic means may generate ultrasonic waves while vibrating, promoting mixing of different fluids in the first mixing chamber 204*a* or the second mixing chamber 204*b*. Or, the ultrasonic means may promote bead dissolution in the solution contained in the first mixing chamber 204*a* or the second mixing chamber 204*b*.

The first mixing chamber 204*a* or the second mixing chamber 204*b* may include a heating element (e.g., Peltier element) to generate heat or may receive heat from the heating means mounted in the target analyte detection device. The heating means may generate heat and transfer it to the first mixing chamber 204*a* or the second mixing chamber 204*b* to increase the temperature inside the first mixing chamber 204*a* or the second mixing chamber 204*b*, promoting the mixing reaction, dissolution reaction, or chemical reaction.

The first mixing chamber 204*a* may be divided into an upper space and a lower space. The upper space and the lower space may be spatially separated while being connected to each other.

The upper space of the first mixing chamber 204*a* may be provided with an inlet through which a fluid is introduced and have the internal control bead 251 (IC bead) and the protease K bead 252. The magnetic bead 253 may be provided in the lower space of the first mixing chamber 204*a* and may be provided as a space in which the sample and the buffer or reagent are mixed. The drain flow path 224 may be connected to the lower space of the first mixing chamber 204*a*.

It is possible to prevent the mixed solution from splashing into the upper space while mixing in the lower space of the first mixing chamber 204*a*. For example, a blocking wall may be provided in a portion except for the passage between the upper space and the lower space of the first mixing chamber 204*a*.

The first mixing chamber 204*a* may be connected to the lysis buffer chamber 261 and the binding buffer chamber 262 through the first buffer flow path 231, be connected to the second washing buffer chamber 264 through the second buffer flow path 232, and be connected to the first washing buffer chamber 263 through the third buffer flow path 233. In this case, the first buffer flow path 231 may be branched and connected to the lysis buffer chamber 261 and the binding buffer chamber 262, respectively.

The first buffer flow path 231 may join the mixing flow path 223. Specifically, the first buffer flow path 231 may join the mixing flow path 223 at the rear end of the point where the flow path connected to the lysis buffer chamber 261 and the flow path connected to the binding buffer chamber 262 meet and connect to the first mixing chamber 204*a*. Accordingly, the flow path from the point where the first buffer flow path 231 and the mixing flow path 223 join to the first mixing chamber 204*a* may be referred to as the first buffer flow path 231 or the mixing flow path 223.

The second mixing chamber 204*b* may be connected to the elution buffer chamber 265 through the fourth buffer flow path 234.

The second mixing chamber 204*b* may be connected to the detection chamber 205 through the detection flow path 235. A fifth valve 245 for opening and closing the detection flow path 235 may be provided.

One end of the detection flow path 235 may be connected to the second mixing chamber 204*b*, and the other end thereof may be connected to each of the plurality of detection chambers 205. The detection flow path 235 may be opened and closed by the fifth valve 245. The detection flow path 235 may be branched into a plurality of branch flow paths corresponding to the plurality of detection chambers 205 at the fifth valve 245 or at the rear end of the fifth valve 245. For example, the detection flow path 235 may be branched into six branch flow paths respectively connected to the six detection chambers 205.

The fifth valve 245 may further include an air collecting space. Air bubbles generated during the mixing process in the second mixing chamber 204*b* may move to the air collection space provided above the fifth valve 245 so that the sample fluid free from air bubbles may be moved through the detection flow path 235.

The plurality of detection chambers 205 may be positioned side by side along the upper and lower directions on the left edge of the base 21. For example, the plurality of detection chambers 205 may be provided close to an end portion where the cartridge 20 is inserted into the detection device. The target analyte detection device may be provided with a detection module capable of inspecting whether the target analyte is present in the detection chambers 205 provided in the inserted cartridge 20. For example, the detection module may include an LED that emits excitation light and a photodiode that receives reflected light reflected from the detection chamber 205.

The detection chamber 205 may include a detection reagent therein. The detection reagent may be prepared in a freeze-dried state. If the sample flows into the detection chamber 205 through the detection flow path 235, a detection reaction may occur as the detection reagent is dissolved.

The target analyte detection device may include a detection chamber heating means for transferring heat to the detection chamber 205. If heat is transferred from the detection chamber heating means, the temperature of the detection chamber 205 is increased to and maintained at a certain temperature so that a detection reaction may occur inside the detection chamber 205.

Each detection chamber 205 may be connected to the detection buffer chamber 206. The detection buffer chamber 206 may be a space for receiving the sample overflowing the detection chamber 205, a space for storing the air of the detection flow path 235 and the detection chamber 205, or a space for storing the gas generated in the detection chamber 205.

The six detection buffer chambers 206 may all have the same volume. As the air is pushed out while the sample fluid moves through the detection flow path 235 and the detection chamber 205 and is stored in each buffer chamber 206, the six detection buffer chambers 206 all may provide the same reaction force. Accordingly, the same amount of sample fluid may be provided to each detection chamber 205.

A process for detecting a target analyte using the cartridge 20 according to an embodiment is described below.

A robot of the target analyte detection device may wait for a user input to execute the protocol.

Sample Loading and Cartridge Mounting

The user may load the sample into the injection space 201*a* of the sample chamber 201. For example, after opening the closure and injecting the sample into the injection space 201*a* through a pipette, the user may close and seal the closure.

The user may seat or insert and mount the cartridge 20 into the insertion portion of the target analyte detection device and then input an operation signal for starting the detection process through the control panel of the detection device. Alternatively, after recognizing the mounting or insertion of the cartridge 20 in the insertion portion, the detection device may perform the protocol after a predetermined time elapses without the user's operation signal.

The robot performs the following protocol.

If the mounting of the cartridge 20 is recognized, the robot arm where the cartridge 20 is mounted clamps the cartridge 20. The robot arm moves the cartridge 20 to the operation position. The operating position of the cartridge 20 may be the same as the detection position. For example, if the cartridge 20 is moved to the operation position, the detection chamber 205 may be positioned below the detection module.

In the initial state before the process of the cartridge 20 is started, all the valves 241 to 245 and the pneumatic flow paths 211 and 213 may be in the open state. However, the sample shutoff valve 246 provided at the outlet or the rear end of the outlet of the liquid feeding space 201*b* may be in the closed state in the initial state. The pressurizing module that applies pressure to the blister chamber may also be in the initial state (open state).

Sample Metering Process

Then, the detection device may perform a metering process of metering a predetermined amount of sample or a quantity of sample in the sample chamber 201.

The valve controller may open the first valve 241 and the third valve 243 while closing the remaining valves. The valve controller may open the sample shutoff valve 246 provided at the rear end of the outlet of the liquid feeding space 201*b* to flow the sample to the sample flow path 221.

The pneumatic controller closes the first pneumatic port 212 and opens the second pneumatic port 214 and may then provide negative pressure through the second pneumatic port 214. The provided negative pressure may be in turn transferred to the second pneumatic flow path 213, the first mixing chamber 204*a*, the drain flow path 224, the third valve 243, the second waste flow path 226, the waste chamber 203, the first waste flow path 225, the metering chamber 202, the metering flow path 222, the sample flow path 221, and the sample chamber 201.

Thereafter, the sample in the sample chamber 201 fills the metering flow path 222 and the metering chamber 202, overflows the metering chamber 202, and then moves until filling a portion of the first waste flow path 225 or may reach through the first waste flow path 225 to the waste chamber 203.

Then, the valve controller may switch the first valve 241 to the closed state. The pneumatic controller opens the first pneumatic port 212 and the second pneumatic port 214 and may then provide positive pressure to the first pneumatic port 212 or negative pressure to the second pneumatic port 214.

The provided positive pressure may be in turn transferred to the first pneumatic flow path 211, the first waste flow path 225, the waste chamber 203, the second waste flow path 226, the third valve 243, the drain flow path 224, the first mixing chamber 204*a*, and the second pneumatic flow path 213.

In this process, the sample remaining in the first waste flow path 225 is discarded to the waste chamber 203. As the sample overflowing the metering chamber 202 is discarded into the waste chamber 203, the volume of the sample filling the metering chamber 202 from the first valve 241 may be metered. The process of removing the overflowed sample through air may be referred to as an air knife process.

Then, the process of transferring the metered sample to the first mixing chamber 204*a* may be performed.

The valve controller may switch the second valve 242 to the open state and may switch the third valve 243 to the closed state. The pneumatic controller may provide positive pressure through the first pneumatic port 212 or negative pressure to the second pneumatic port 214.

The provided positive pressure may be in turn transferred to the first pneumatic flow path 211, the metering chamber 202, the metering flow path 222, the second valve 242, the mixing flow path 223, and the first mixing chamber 204*a*. In this process, the sample filling the metering chamber 202 may be transferred to the first mixing chamber 204*a* through the second valve 242 and the mixing flow path 223.

The internal control bead 252 positioned inside the first mixing chamber 204*a* may be dissolved in the sample transferred to the first mixing chamber 204*a*.

Lysis Process

Next, the lysis buffer is transferred to the first mixing chamber 204*a*, and the lysis process may be performed in the first mixing chamber 204*a*.

The valve controller may switch the second valve 242 to the closed state to close all the valves. The pneumatic controller may close the first pneumatic port 212 and provide negative pressure through the second pneumatic port 214. The provided negative pressure may in turn be transferred to the second pneumatic flow path 213 and the first buffer flow path 231.

The blister pressurizing means may simultaneously pressurize the lysis buffer chamber 261 to supply the lysis buffer. In this process, the lysis buffer of the lysis buffer chamber 261 is transferred to the mixing flow path 223 through the first buffer flow path 231. The protease K bead 252 positioned in the first mixing chamber 204*a* may be dissolved in the lysis buffer.

The ultrasonic means generates ultrasonic waves in the first mixing chamber 204*a* to mix the sample and the lysis buffer.

The pneumatic controller may provide positive pressure through the second pneumatic port 214. Since all the valves are closed, the positive pressure may increase the pressure in the first mixing chamber 204*a*. The heating means may apply heat to the first mixing chamber 204*a* to increase the temperature in the chamber.

As such, an incubating process may be performed for a predetermined time with the pressure and temperature of the first mixing chamber 204*a* increased.

Binding Process

Next, the binding buffer is transferred to the first mixing chamber 204*a*, and the binding process may be performed in the first mixing chamber 204*a*.

The pneumatic controller may provide negative pressure through the second pneumatic port 214. The provided negative pressure may in turn be transferred to the second pneumatic flow path 213, the first mixing chamber 204*a*, and the first buffer flow path 231.

The blister pressurizing means may simultaneously pressurize the binding buffer chamber 262 to supply the binding buffer. In this process, the binding buffer of the binding buffer chamber 262 is transferred to the first mixing chamber 204*a* through the first buffer flow path 231.

Then, the valve controller may switch the second valve 242 to the open state to open the mixing flow path 223. The pneumatic controller may provide positive pressure through the first pneumatic port 212. The provided positive pressure may in turn be transferred to the first pneumatic flow path 211, the metering chamber 202, the metering flow path 222, the second valve 242, the first buffer flow path 231, the first mixing chamber 204*a*, and the second pneumatic flow path 213. In this process, the binding buffer remaining in the first buffer flow path 231 may be completely discharged to the first mixing chamber 204*a*.

Then, the valve controller may switch the second valve 242 to the closed state to close all the valves. The pneumatic controller may close both the first pneumatic port 212 and the second pneumatic port 214.

The ultrasonic means generates ultrasonic waves in the first mixing chamber 204*a* to mix the sample and the binding buffer. The heating means applies heat to the first mixing chamber 204*a* and incubates for a predetermined time. After a certain time elapses and the binding process is completed, the magnetic means generates an electromagnetic field to collect the magnetic beads 253.

Then, a drain process of the first mixing chamber 204*a* may be performed. The valve controller may switch the third valve 243 to the open state to open the drain flow path 224. The pneumatic controller may provide negative pressure through the first pneumatic port 212 or positive pressure through the second pneumatic port 214.

In this process, the solution in the first mixing chamber 204*a* is dumped into the waste chamber 203 through the drain flow path 224, the third valve 243, and the second waste flow path 226. In this case, the magnetic bead 253 remains attached to the magnetic means.

First Washing Process

Then, a first washing buffer is transferred to the first mixing chamber 204*a*, and a first magnetic bead washing process may proceed.

The pneumatic controller may shut off the first pneumatic port 212 and provide negative pressure through the second pneumatic port 214. The valve controller may switch the third valve 243 to the closed state to close all the valves.

The blister pressurizing means may simultaneously pressurize the first washing buffer chamber 263 to supply the washing buffer. In this process, the first washing buffer of the first washing buffer chamber 263 is transferred to the first mixing chamber 204*a* through the second buffer flow path 232.

The magnetic means stops the operation, and the magnetic bead 253 attached to the magnetic means is detached in the first mixing chamber 204*a*. The ultrasonic means generates ultrasonic waves in the first mixing chamber 204*a* to mix the magnetic beads 253 and the first washing buffer. The heating means applies heat to the first mixing chamber 204*a* and incubates for a predetermined time. After a certain time elapses and the first washing process is completed, the magnetic means generates an electromagnetic field to collect the magnetic beads 253.

Then, a drain process of the first mixing chamber 204*a* may be performed. The valve controller may switch the third valve 243 to the open state to open the drain flow path 224. The pneumatic controller may provide negative pressure through the first pneumatic port 212 or positive pressure through the second pneumatic port 214.

In this process, the solution in the first mixing chamber 204*a* is dumped into the waste chamber 203 through the drain flow path 224, the third valve 243, and the second waste flow path 226. In this case, the magnetic bead 253 remains attached to the magnetic means.

Second Washing Process

Then, a second washing buffer is transferred to the first mixing chamber 204*a*, and a second magnetic bead washing process may proceed.

The pneumatic controller may shut off the first pneumatic port 212 and provide negative pressure through the second pneumatic port 214. The valve controller may switch the third valve 243 to the closed state to close all the valves.

The blister pressurizing module may simultaneously pressurize the second washing buffer chamber 264 to supply the washing buffer. In this process, the second washing buffer of the second washing buffer chamber 264 is transferred to the first mixing chamber 204*a* through the third buffer flow path 233.

The magnetic means stops the operation, and the magnetic bead 253 attached to the magnetic means is detached in the first mixing chamber 204*a*. The ultrasonic means generates ultrasonic waves in the first mixing chamber 204*a* to mix the magnetic beads 253 and the second washing buffer. The heating means applies heat to the first mixing chamber 204*a* and incubates for a predetermined time. After a certain time elapses and the second washing process is completed, the magnetic means of the detection device is operated to collect the magnetic beads 253.

Then, a drain process of the first mixing chamber 204*a* may be performed. The valve controller may switch the third valve 243 to the open state to open the drain flow path 224. The pneumatic controller may provide negative pressure through the first pneumatic port 212 or positive pressure through the second pneumatic port 214.

In this process, the solution in the mixing chamber 204 is dumped into the waste chamber 203 through the drain flow path 224 and the second waste flow path 226. In this case, the magnetic bead 253 remains attached to the magnetic means.

Even after the drain flow path 224 and the second waste flow path 226 are emptied, pneumatic pressure may be continuously provided to dry the drain flow path 224 and the second waste flow path 226.

Elution Process

Then, an elution process of the first mixing chamber 204*a* may be performed.

The pneumatic controller may shut off the first pneumatic port 212 and provide negative pressure through the second pneumatic port 214. The valve controller may maintain all the valves in the closed state.

The blister pressurizing means may simultaneously pressurize the elution buffer chamber 265 to supply the elution buffer. In this process, the elution buffer of the elution buffer chamber 265 is transferred to the first mixing chamber 204*a* through the fourth buffer flow path 234.

The pneumatic controller blocks the first pneumatic port 212 and provides negative pressure through the second pneumatic port 214 to vent the evaporated gas in the first mixing chamber 204*a*.

The magnetic means stops the operation, and the magnetic bead 253 attached to the magnetic means is detached in the first mixing chamber 204*a*. The ultrasonic means generates ultrasonic waves in the first mixing chamber 204*a* to mix the magnetic beads 253 and the elution buffer.

The pneumatic controller may provide positive pressure through the second pneumatic port 214. Since all the valves are closed, the positive pressure may increase the pressure in the first mixing chamber 204*a*. The heating means may apply heat to the first mixing chamber 204*a* to increase the temperature in the chamber. As such, an incubating process may be performed for a predetermined time with the pressure and temperature of the first mixing chamber 204*a* increased.

After a certain time elapses and the second washing process is completed, the magnetic means of the detection device is operated to collect the magnetic beads 253.

Master Mix Process

Next, a master mix process of transferring the eluted sample solution from the first mixing chamber 204*a* to the second mixing chamber 204*b* and mixing it with the master mix may be performed.

The pneumatic controller may provide negative pressure through the first pneumatic port 212 or positive pressure through the second pneumatic port 214. The valve controller may switch the fourth valve 244 to the open state.

The first mixing chamber 204*a* is connected to the second mixing chamber 204*b* through the master mix flow path 227 and the fourth valve 244. In this process, the eluted sample solution of the first mixing chamber 204*a* is transferred to the second mixing chamber 204*b* through the master mix flow path 227.

The valve controller may switch the fourth valve 244 to the closed state. The ultrasonic means may generate ultrasonic waves in the second mixing chamber 204*b* to mix the eluted sample solution and the master mix. The heating means may apply heat to the second mixing chamber 204*b* and incubate for a predetermined time.

The valve controller may switch the fourth valve 244 to the open state and may vent the gas generated in the second mixing chamber 204*b* through the master mix flow path 227.

Detection Process

Next, a pre-detection process of transferring the buffer mixed with the master mix in the second mixing chamber 204*b* to the detection chamber 205 may be performed.

The valve controller may switch the fourth valve 244 and fifth valve 245 to the open state to open the master mix flow path 227 and detection flow path 235. The pneumatic controller may block the first pneumatic port 212 and provide positive pressure through the second pneumatic port 214. The provided positive pressure may in turn be transferred to the second pneumatic flow path 213, the first mixing chamber 204*a*, the master mix flow path 227, the second mixing chamber 204*b*, and the detection flow path 235. In this process, the solution mixed with the master mix in the second mixing chamber 204*b* is transferred to the detection chamber 205.

Then, a detection reaction may occur in the detection chamber 205 and a detection process may proceed.

The valve controller may switch the fifth valve 245 to the closed state. The solution transferred from the second mixing chamber 204*b* to the detection chamber 205 through the detection flow path 235 may dissolve the beads in the detection chamber 205.

The detection chamber heating means may apply heat to the detection chamber 205 to perform a PCR reaction for a predetermined time. The PCR reaction may be performed at a predetermined temperature for a predetermined time, and a plurality of reactions may proceed at two or more temperatures.

The pressure increased while the detection chamber 205 is heated may be released to the detection buffer chamber 206. For example, the gas generated in the detection chamber 205 may move to the detection buffer chamber 206.

Then, if the detection reaction is completed, the detection module detects the target analyte in the detection chamber 205. For example, the detection module may generate detection light and emit the detection light to the detection chamber 205 and receive reflected light reflected from the target analyte to inspect the target analyte.

Finally, before the cartridge 20 on which the detection process is completed is removed from the detection device, a process of releasing the pressure of the cartridge 20 may be performed. The pneumatic controller provides negative pressure through the second pneumatic port 214, and the valve controller switches the fifth valve 245 to the open state to open the detection flow path 235. The fourth valve 244 is maintained in the open state, so that the master mix flow path 227 is also in the open state.

In this process, the gas of the detection chamber 205 and the detection flow path 235 is vented to the second pneumatic port 214.

Cartridge Removal

After all the reactions are finished, the valve controller switches all the valves to the open state, and the pneumatic controller opens the first and second pneumatic ports 212 and 214.

The cartridge 20 may be removed from the detection device.

The above-described embodiments are merely examples, and it will be appreciated by one of ordinary skill in the art various changes may be made thereto without departing from the scope of the disclosure. Accordingly, the embodiments set forth herein are provided for illustrative purposes, but not to limit the scope of the disclosure, and should be appreciated that the scope of the disclosure is not limited by the embodiments. The scope of the disclosure should be construed by the following claims, and all technical spirits within equivalents thereof should be interpreted to belong to the scope of the disclosure.

LEGEND OF REFERENCE NUMBERS

10, 20: target analyte detection cartridge
11, 21: base, 12, 22: blister chamber unit,
11*a*: pre-processing region, 11*b*: detection region,
11*c*: sample flow region, 11*d*: blister chamber region,
100, 200: base plate, 101, 201: sample chamber,
102, 202: metering chamber, 103, 203: waste chamber,
104, 204: mixing chamber, 105, 205: detection chamber,
106, 206: detection buffer chamber,
111, 211: first pneumatic flow path, 112, 212: first pneumatic port,
113, 213: second pneumatic flow path, 114, 214: second pneumatic port,
121, 221: sample flow path, 122, 222: metering flow path,
123, 223: mixing flow path, 124, 224: drain flow path,
125, 225: first waste flow path, 126, 226: second waste flow path,
127: buffer drain flow path, 227: master mix flow path,
131, 231: first buffer flow path, 132, 232: a second buffer flow path,
233: third buffer flow path, 234: fourth buffer flow path,
133, 235: detection flow path,
141-145, 241-245: first to fifth valves,
246: sample shutoff valve,
151, 251: internal control bead, 152, 252: protease K bead,
153, 253: magnetic bead,
161, 261: lysis buffer chamber, 162, 262: binding buffer chamber,
163,164, 263, 264: washing buffer chamber, 165, 265: elution buffer chamber,
170, 270: blister plate, 171, 271: first blister chamber;
172, 272: second blister chamber, 173, 273: blister connection passage,
174: first blister membrane, 175: second blister membrane,
176: pin.

What is claimed is:

1. A cartridge for detecting a target analyte, comprising:
a sample chamber into which sample is inserted;
a metering chamber connected to the sample chamber to meter a predetermined amount of sample;
a mixing chamber connected to the metering chamber to receive magnetic beads;
a waste chamber connected to the metering chamber;
a plurality of buffer chambers connected to the mixing chamber to receive a buffer;
a detection chamber connected to the mixing chamber to detect the target analyte;
a metering flow path connecting the sample chamber and the metering chamber;
a waste flow path connecting the metering chamber and the waste chamber;
a mixing flow path connecting the metering chamber and the mixing chamber;
a plurality of buffer flow paths connecting each buffer chamber and the mixing chamber;
a detection flow path connecting the mixing chamber and the detection chamber;
a first pneumatic flow path communicating with a first pneumatic port;
a second pneumatic flow path communicating with a second pneumatic port,
a first valve configured to open and close the metering flow path;
a second valve configured to open and close the mixing flow path and to be driven independently of the first valve;
a chamber region in which the sample chamber, the metering chamber, and the mixing chamber are disposed;
a valve region in which the first and second valves are disposed;
a buffer region in which the plurality of buffer chambers are disposed;
a pre-processing region comprising the chamber region, the valve region, and the buffer region; and
a detection region in which the detection chamber is disposed,
wherein the pre-processing region and the detection region are arranged in a horizontal direction and mutually non-overlapping in the horizontal direction, wherein the chamber region, the valve region, and the buffer region within the pre-processing region are sequentially arranged in a vertical direction and mutually non-overlapping in the vertical direction,
wherein the sample chamber, the metering chamber, and the mixing chamber within the chamber region are sequentially arranged in the horizontal direction,
wherein the plurality of buffer chambers are disposed lower than the mixing chamber in the gravitational direction when the cartridge is mounted in a detection device, and each of the plurality of buffer chambers is a blister chamber configured to transfer a contained buffer when pressure is applied, and
wherein when the cartridge is in a standing state in which a top of the cartridge is positioned up, the vertical direction extends from the top of the cartridge to the bottom of the cartridge, and the horizontal direction extends from one side of the cartridge to the other side of the cartridge.

2. The cartridge of claim 1, further comprising:
a drain flow path connecting the mixing chamber and the waste chamber; and
a third valve configured to open and close the drain flow path;
wherein the valve region further comprises the third valve; and
wherein in the valve region, the first valve, the second valve, and the third valve are arranged side by side in the horizontal direction.

3. The cartridge of claim 2, further comprising:
a mastermix chamber provided in the pre-processing region and having one side connected to the mixing chamber and another side connected to the detection chamber;
a fourth valve controlling a fluid flow between the mixing chamber and the mastermix chamber; and a fifth valve controlling a fluid flow between the mastermix chamber and the detection chamber.

4. The cartridge of claim 1, wherein the plurality of buffer chambers include a lysis buffer chamber, a binding buffer chamber, a washing buffer chamber, and an elution buffer chamber, and wherein in the buffer region, the plurality of buffer chambers are arranged side by side in the horizontal direction.

5. The cartridge of claim 1, wherein the sample chamber, the metering chamber, and the mixing chamber, and the detection chamber are sequentially disposed.

6. The cartridge of claim 1, wherein the sample chamber has a shape in which a width in the vertical direction is larger than a width in the horizontal direction and includes an injection space provided in an upper portion of the sample chamber in the vertical direction and a liquid delivery space provided in a lower portion of the sample chamber in the vertical direction and connected to the metering chamber.

7. The cartridge of claim 1, wherein the metering chamber has a shape in which a width in the vertical direction is larger than a width in the horizontal direction, and wherein an upper portion of the metering chamber in the vertical direction is connected to the waste flow path, and a lower portion of the metering chamber in the vertical direction is connected to each of the sample chamber and the mixing chamber.

8. The cartridge of claim 1, wherein the detection chamber comprises:

a plurality of detection chambers arranged side by side in the vertical direction.

9. The cartridge of claim 1, wherein the waste chamber is positioned lower than the sample chamber, the metering chamber, and the mixing chamber in the vertical direction.

10. The cartridge of claim 9, wherein a waste region where the waste chamber is provided is disposed below the buffer region.

11. The cartridge of claim 1, wherein one side of the metering chamber is connected to each of the sample chamber and the mixing chamber, and another side thereof is connected to the waste chamber, and wherein the first pneumatic flow path joins the other side of the metering chamber and then is connected to the waste flow path.

12. The cartridge of claim 1, further comprising a mastermix chamber provided in the pre-processing region and having one side connected to the mixing chamber and another side connected to the detection chamber.

13. The cartridge of claim 12, wherein the first pneumatic flow path is divided into a first branch connected to the metering chamber and the waste chamber and a second branch connected to the mastermix chamber, and wherein the second pneumatic flow path is connected to the mixing chamber.

14. The cartridge of claim 1, wherein, when the cartridge is mounted on the target analyte detection device in the standing state, the top of the cartridge faces upward and the bottom of the cartridge faces downward.

* * * * *